(12) United States Patent
Menz et al.

(10) Patent No.: US 12,186,593 B2
(45) Date of Patent: Jan. 7, 2025

(54) PATTERN INTERFERENCE RADIATION FORCE (PIRF) NEURAL STIMULATORS

(71) Applicant: The Board of Trustees of the Leland Stanford Junior University, Stanford, CA (US)

(72) Inventors: Michael D. Menz, San Bruno, CA (US); Butrus T. Khuri-Yakub, Palo Alto, CA (US); Stephen A. Baccus, Half Moon Bay, CA (US); Patrick Ye, Palo Alto, CA (US); Kim Pauly, Stanford, CA (US); Kamyar Firouzi, San Jose, CA (US); Morten F. Rasmussen, San Francisco, CA (US); Omer Oralkan, Morrisville, NC (US); Amin Nikoozadeh, San Carlos, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 705 days.

(21) Appl. No.: 16/894,421

(22) Filed: Jun. 5, 2020

(65) Prior Publication Data

US 2020/0384292 A1    Dec. 10, 2020

Related U.S. Application Data

(60) Provisional application No. 62/858,884, filed on Jun. 7, 2019.

(51) Int. Cl.
*A61N 7/00* (2006.01)
*A61M 21/00* (2006.01)

(52) U.S. Cl.
CPC .............. *A61N 7/00* (2013.01); *A61M 21/00* (2013.01); *A61M 2021/0011* (2013.01); *A61N 2007/0026* (2013.01); *A61N 2007/0078* (2013.01)

(58) Field of Classification Search
CPC .............. A61N 7/00; A61N 2007/0026; A61N 2007/0078; A61N 2007/0069;
(Continued)

(56) References Cited

U.S. PATENT DOCUMENTS

| | | | | |
|---|---|---|---|---|
| 4,343,301 A | * | 8/1982 | Indech | G01H 13/00 601/3 |
| 2003/0014093 A1 | * | 1/2003 | Makin | A61B 8/12 607/96 |

(Continued)

OTHER PUBLICATIONS

Prospects for transcranial temporal interference stimulation in humans: a computational study Sumientra Rampersad, Biel Roig-Solvas, Mathew Yarossi, Praveen P. Kulkarni, Emiliano Santarnecchi, Alan D. Dorval, Dana H. Brooks bioRxiv 602102; doi: https://doi.org/10.1101/602102 (Year: 2019).*

(Continued)

*Primary Examiner* — Pascal M Bui Pho
*Assistant Examiner* — Michael Yiming Fang
(74) *Attorney, Agent, or Firm* — LUMEN PATENT FIRM

(57) ABSTRACT

Improved acoustic neurostimulation is provided by having two or more acoustic transducers generate an acoustic interference pattern in a region of a patient being treated. The apparatus has at least two operating modes it can switch between. A first operating mode has the transducers driven at the same frequency. A second operating mode has the transducers driven at different frequencies. Full control of the acoustic transducers allows the acoustic interference pattern to be varied electronically at will.

18 Claims, 13 Drawing Sheets

(58) Field of Classification Search
CPC .......... A61N 2007/0073; A61M 21/00; A61M 2021/0011; A61M 2205/3306
See application file for complete search history.

(56) References Cited

U.S. PATENT DOCUMENTS

| | | | |
|---|---|---|---|
| 2005/0020945 A1* | 1/2005 | Tosaya | A61N 7/00 601/2 |
| 2006/0241529 A1* | 10/2006 | Hynynen | A61B 8/0816 601/2 |
| 2009/0099485 A1* | 4/2009 | Sarvazyan | A61N 7/00 601/2 |
| 2009/0112133 A1* | 4/2009 | Deisseroth | A61N 7/00 601/3 |
| 2010/0160779 A1* | 6/2010 | Browning | A61B 5/02007 600/454 |
| 2011/0130615 A1 | 6/2011 | Mishelevich | |
| 2012/0053391 A1 | 3/2012 | Mishelevich | |
| 2012/0283502 A1 | 11/2012 | Mishelevich | |
| 2012/0289869 A1* | 11/2012 | Tyler | A61N 7/00 601/2 |
| 2013/0131495 A1 | 5/2013 | Konofagou | |
| 2013/0245505 A1 | 9/2013 | Khuri-Yakub | |
| 2014/0058292 A1* | 2/2014 | Alford | A61N 7/00 601/2 |
| 2015/0151142 A1* | 6/2015 | Tyler | A61B 6/03 601/2 |
| 2017/0258386 A1* | 9/2017 | Woltjer | A61F 5/48 |
| 2018/0193675 A1* | 7/2018 | Vortman | A61N 7/02 |
| 2019/0308038 A1* | 10/2019 | Prus | A61N 7/02 |
| 2021/0204915 A1* | 7/2021 | Vortman | A61N 7/02 |
| 2021/0346725 A1* | 11/2021 | Rousso | A61N 7/02 |

OTHER PUBLICATIONS

Lenshof, Andreas & Evander, Mikael & Laurell, T & Nilsson, Johan. (2012). Acoustofluidics 5: Building microfluidic acoustic resonators. Lab on a chip. 12. 684-95. 10.1039/c1lc20996e (Year: 2012).*

Urban M. W., Bernal M., and Greenleaf J. F., "Phase aberration correction using ultrasound radiation force and vibrometry optimization," in IEEE Transactions on Ultrasonics, Ferroelectrics, and Frequency Control, vol. 54, No. 6, pp. 1142-1153, Jun. 2007, doi: 10.1109/TUFFC.2007.368 (Year: 2007).*

Kim et al., "Improved Target Specificity of Transcranial Focused Ultrasound Stimulation (TFUS) using Double-Crossed Ultrasound Transducers", 2018, Conf Proc IEEE Eng Med Biol Soc, Jul. 2018:2679-2682.

Mehic et al., "Increased Anatomical Specificity of Neuromodulation via Modulated Focused Ultrasound", 2014, PLOS ONE v9n2, e86939.

Menz et al., "Physical mechanisms of ultrasonic neurostimulation of the retina", 2017, bioRxiv preprint.

* cited by examiner

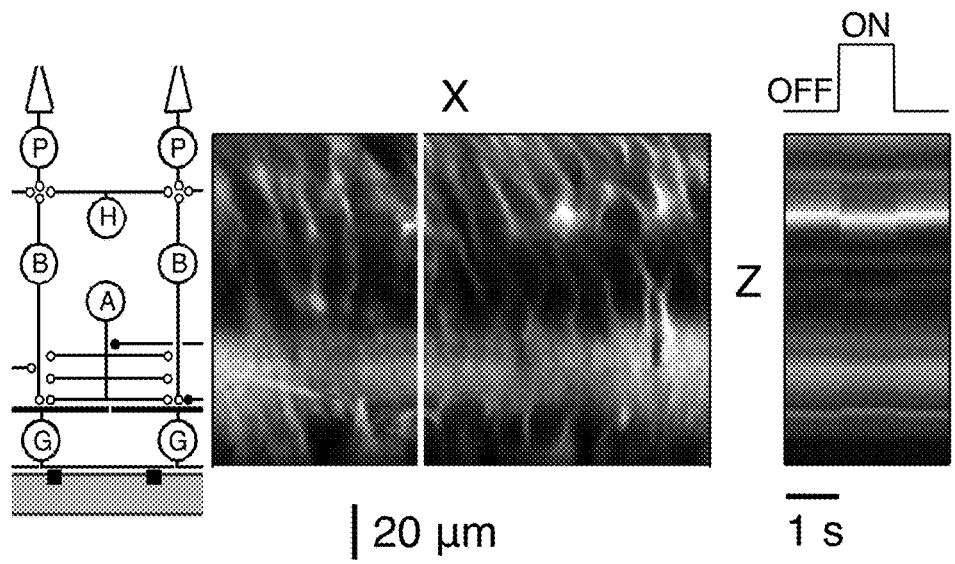
FIG. 5A
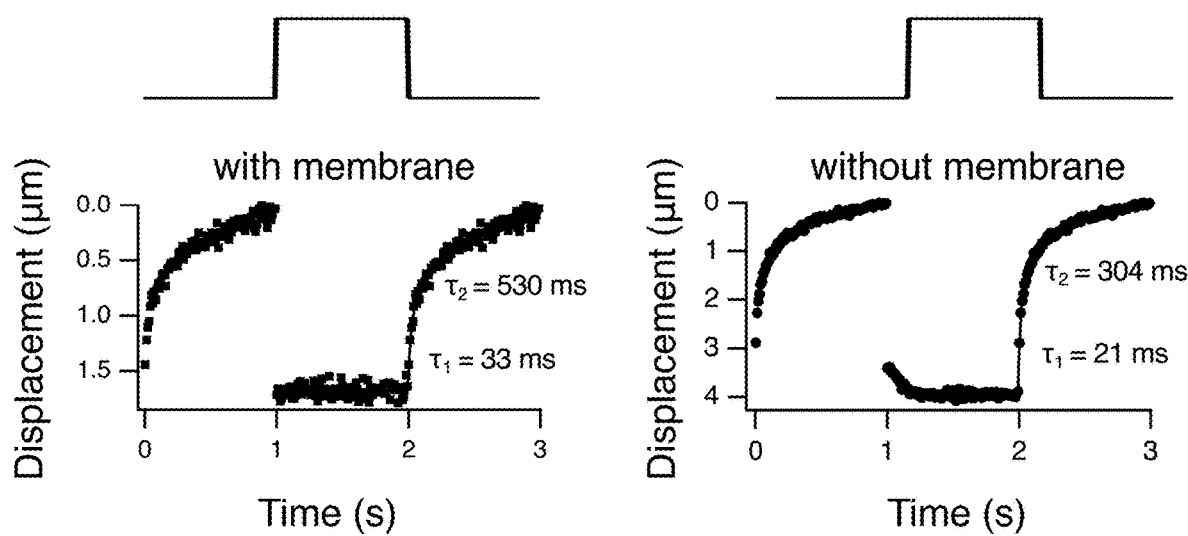
FIG. 5B
FIG. 5C

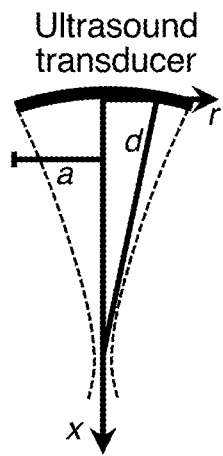
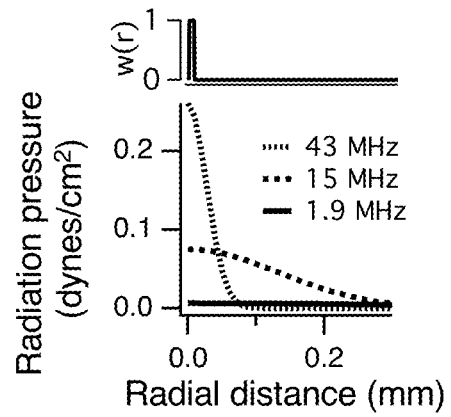
FIG. 8A  FIG. 8B
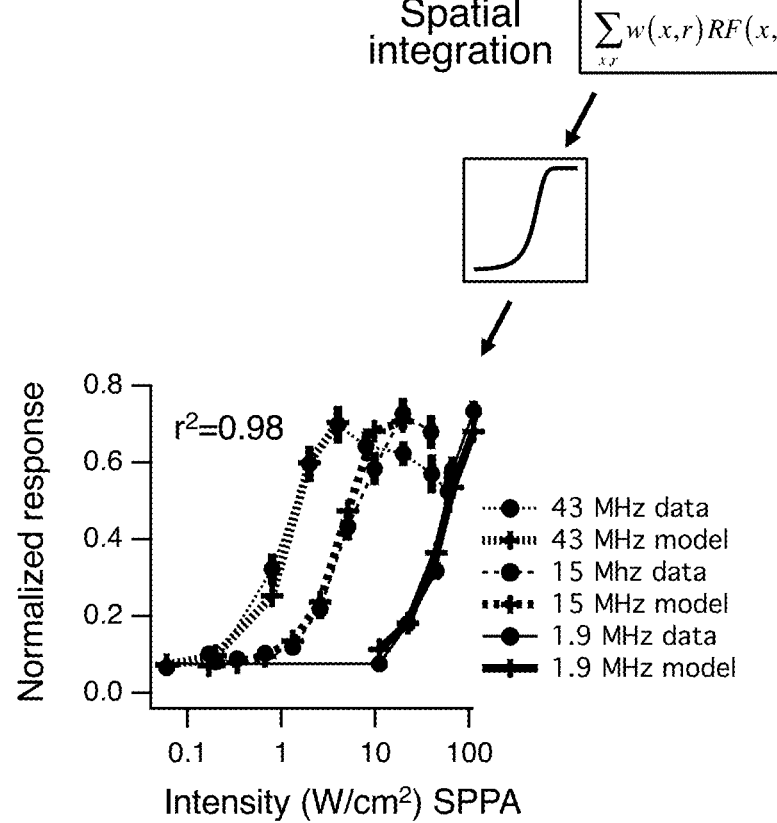
FIG. 8C

PATTERN INTERFERENCE RADIATION FORCE (PIRF) NEURAL STIMULATORS

CROSS REFERENCE TO RELATED APPLICATIONS

This application claims priority from U.S. Provisional Patent Application 62/858,884 filed Jun. 7, 2019, which is incorporated herein by reference.

GOVERNMENT SPONSORSHIP

This invention was made with Government support under contract EB019005 awarded by the National Institutes of Health. The Government has certain rights in the invention.

FIELD OF THE INVENTION

This invention relates to acoustic neurostimulation.

BACKGROUND

There are a large number of neurological diseases and injuries (too numerous to list here) where neurostimulation is potentially beneficial either to cure the patient or resulting in a significant improvement in the quality of their lives. The essential problem with implementing neurostimulation on a large scale is that the conventional method of achieving neurostimulation requires surgical implantation of electrodes in close proximity to the target volume. There are many possible undesirable complications with surgical implantation of electrodes next to neural tissue, most common is the risk of infection, which could be very serious. Therefore, it is desirable to have a method of neurostimulation that is non-invasive.

Currently, the leading candidate technologies are TMS (Transcranial Magnetic Stimulation) and tDCS (transcranial Direct Current Stimulation). Both methods achieve electrical stimulation non-invasively instead of surgically implanted electrodes. However, the problem with these technologies is that the spatial resolution is very poor (i.e., the target tissue is necessarily quite large) and these methods cannot target tissues deep in the human brain.

An alternative technology is to use low-power focused ultrasound, which can reach any arbitrary target tissue in the brain, regardless of depth. It also has high spatial-temporal resolution compared to the other non-invasive methods. Ultrasonic neurostimulation is a relatively new technology and the mechanisms and optimal stimulus parameters are still unknown. In the published literature scientists typically use a single transducer. Compared to other non-invasive methods, such as transcranial magnetic stimulation (TMS), ultrasonic neuro-stimulation has the advantage that it can reach deep into the brain or other tissue with higher spatial resolution and still maintain high temporal resolution. The conventional approach to achieving ultrasonic neuro-stimulation is to use a single transducer or a transducer array that is focused on the target volume.

SUMMARY

An aspect of this work is to optimize the effectiveness (i.e., achieve therapeutic levels of stimulation with minimum power) and spatial specificity (i.e., limit stimulation to small targeted volumes) by creating an interference pattern between at least two transducers. It is a common practice to use multiple transducers in an array to decrease the focal volume, but that is not what we are describing in this invention. Rather, it is the interference pattern between two or more ultrasonic waves that occurs under very specific conditions that achieves more effective stimulation in a smaller volume.

The approach of this work is born from ex vivo research and a radiation force theory of ultrasonic neurostimulation. It strongly suggests using two transducers opposed to one another, such that the interference pattern generated will either produce standing waves (the frequencies are the same) or a beat pattern (the frequencies are slightly different) that will result in much more effective stimulation (less power to achieve a given level of stimulation, or more stimulation for a given power level). It also has the potential to stimulate smaller volumes. These different interference patterns will produce different space-time patterns of mechanical strain arising from radiation force that will alter neurostimulation. For any given medical condition, it is currently unknown exactly what type of neurostimulation is most effective. This approach is intended to optimize ultrasonic neurostimulation by giving clinicians and researchers the flexibility to try different methods of stimulation on the patient to discover what works best for that patient and disease. This will enable translation of this technology from a research novelty to a versatile clinical tool. The device is noninvasive or minimally invasive and can be used for many applications to change the activity of biological tissues including the nervous system.

This approach could be used on any part of the nervous system, central or peripheral, including all sensory systems. It might be used to stimulate, inhibit or modulate neural activity for the purpose of treating various nervous disorders, too numerous to explicitly list here. There are various ultrasound stimulation parameters such a carrier frequency, pulse repetition frequency, duty cycle, intensity, pulse duration and time in between pulses that can be varied to obtain optimal values for a given clinical condition. In the case of two transducers there are additional parameters that specify the relationship between the two transducers, such as phase. Furthermore, the second transducer may operate at a different carrier frequency from the first transducer and other parameters may be different.

Particularly preferred embodiments provide the capability to switch at will between at least three operating modes: 1) standing wave mode with the two transducers operating at the same frequency, 2) oscillating mode with the two transducers operating at different frequencies, and 3) impulse mode from one of the two transducers only.

There are a multitude of possible medical applications, such as depression, Parkinson's, tremor, dystonia, Epilepsy, pain management, and prosthetic devices for sensory systems. For any condition in which electrical neural stimulation is therapeutic, ultrasonic neurostimulation is a possible non-invasive substitute. This could be in the central or peripheral nervous systems, including sensory systems.

Significant advantages are provided. Compared to conventional electrical stimulation, ultrasonic neurostimulation is non-invasive. Non-invasive methods have less risk and cost because no surgery is involved. This makes it much more attractive to patients. The other non-invasive methods of neurostimulation, TMS (transcranial magnetic stimulation) and tDCS (transcranial direct current stimulation) have poor spatial resolution and cannot reach deep into the brain. The conventional method of ultrasonic stimulation, as shown in the literature, uses a single transducer. We use two transducers opposed to one another such that the resulting interference pattern is optimal for stimulation.

Here ultrasonic neural stimulation is defined as any combination of stimulation, inhibition and/or modulation of neural activity.

BRIEF DESCRIPTION OF THE DRAWINGS

FIGS. 5A-C show dynamics of ultrasonic displacement.

FIGS. 8A-C show results of a radiation force model.

DETAILED DESCRIPTION

Section A describes general principles relating to embodiments of the invention. Section B is a detailed scientific study supporting the radiation force model of acoustic neurostimulation.

A) General Principles

A1) Exemplary Embodiments

Figure 1A:
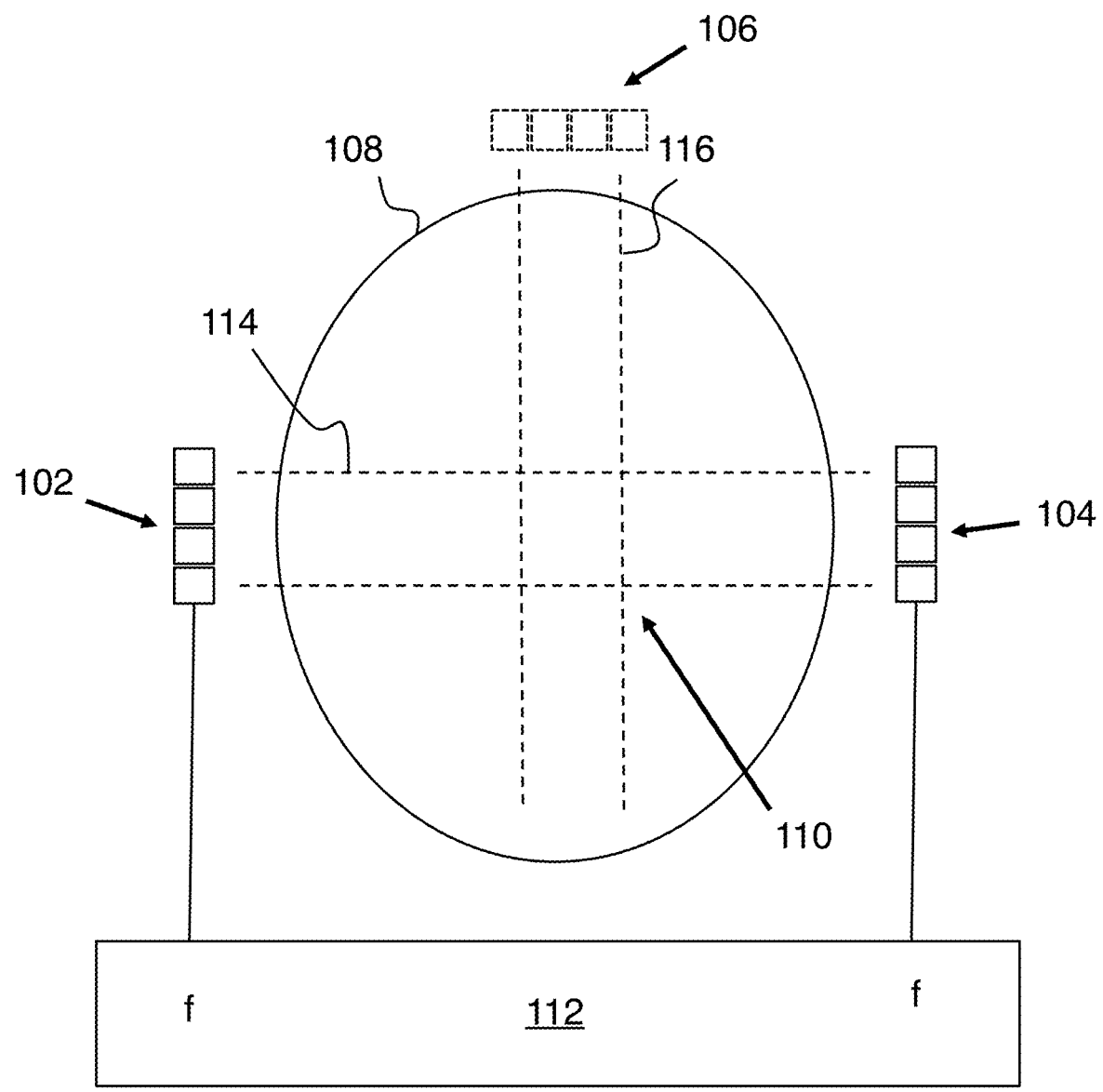
FIGS. 1A-C show three operating modes of an exemplary embodiment of the invention.
Figure 1B:
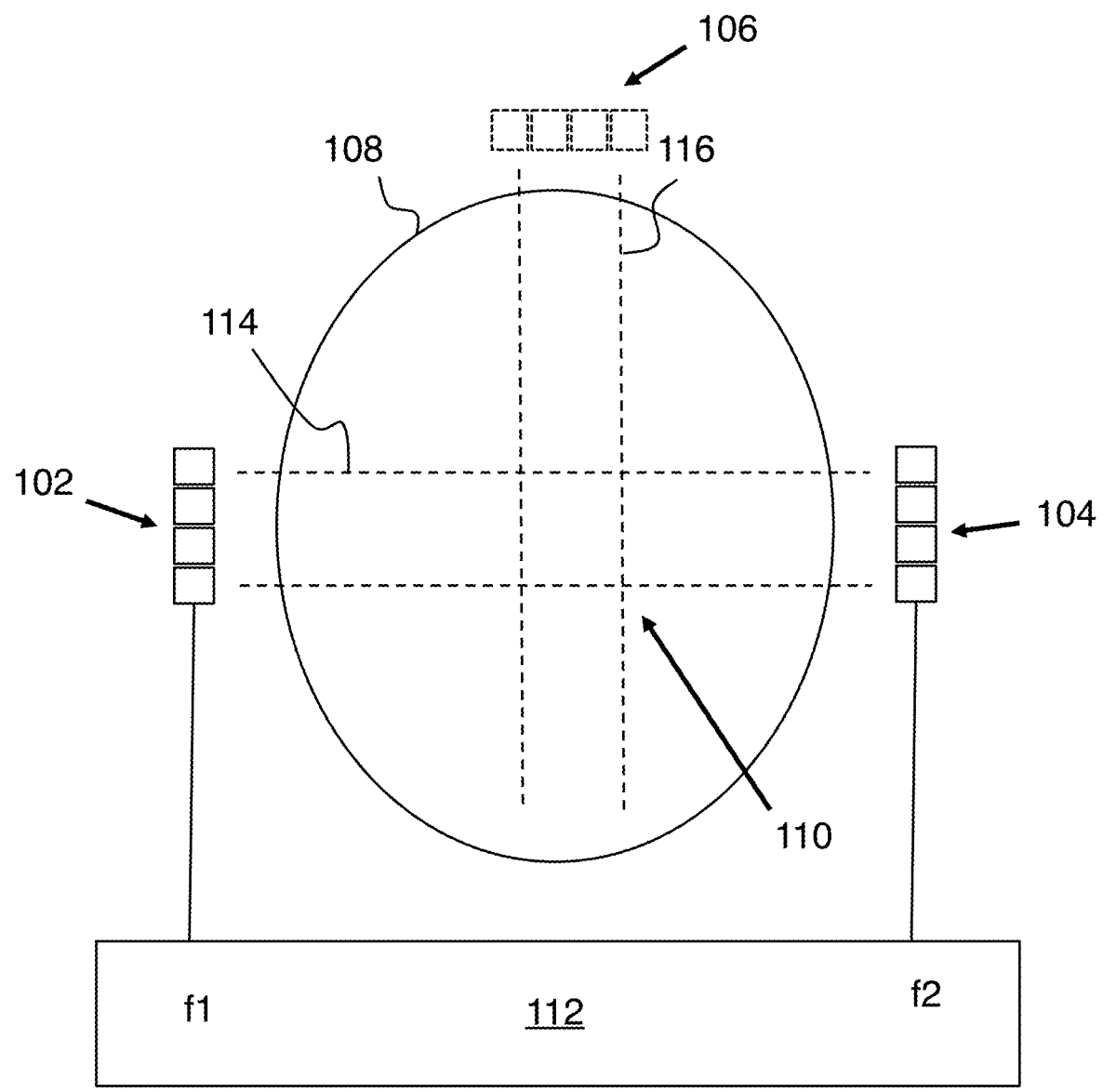

FIGS. 1A-B show an exemplary embodiment of the invention. This example is apparatus for modifying neural activity where the apparatus includes two or more acoustic transducers (102, 104, optionally 106) configured to have their acoustic outputs overlap in a region 110 of a patient 108 under treatment. A controller 112 is configured to control operation of the acoustic transducers. Here the acoustic beam line for transducers 102 and 104 is referenced as 114, while the beam line for transducer 106 is referenced as 116.

The controller is configured to allow a user of the apparatus to select from at least a first operating mode and a second operating mode. Here the first operating mode (FIG. 1A) is a standing wave mode where the acoustic outputs are at the same frequency (f). In this first mode, the frequency f can be time-independent or time-varying. Similarly, the relative phase of the acoustic outputs in the first operating mode can be time-independent or time-varying.

The second operating mode (FIG. 1B) is an oscillating mode where the acoustic outputs have pairwise frequency differences in a range from 1 kHz to 100 kHz. In the example of FIG. 1B, frequencies f1 and f2 have a frequency difference in a range from 1 kHz to 100 kHz. Preferably this frequency difference is in a range from 10 kHz to 100 kHz and more preferably this frequency difference is in a range from 20 kHz to 100 kHz. In this second mode the frequency difference(s) can be time-varying or time-independent. In the case of a time-independent frequency difference, the frequencies f1 and f2 can be time-varying (with fixed frequency difference) or time-independent. Preferably, the pairwise frequency differences of the acoustic outputs in the second operating mode are selected to maximize dynamic radiation force in the region of the patient.

The controller is configured to drive the two or more acoustic transducers independently of each other. This provides electronic control of an acoustic interference pattern generated by the two or more acoustic sources that is provided in the region of the patient.

Preferably some or all of transducers 102, 104, 106 (optional) are acoustic transducer arrays, as schematically shown. Such transducer arrays can be configured to alter a focus position of the acoustic transducer array using phase control of elements of the acoustic transducer array. Such transducer arrays are well known in the art, and so are not further described here.

The apparatus can be configured to modify neural activity in the central nervous system and/or in the peripheral nervous system. Modifying neural activity can include stimulating neural activity, inhibiting neural activity and modulating neural activity in any combination.

Figure 1C:
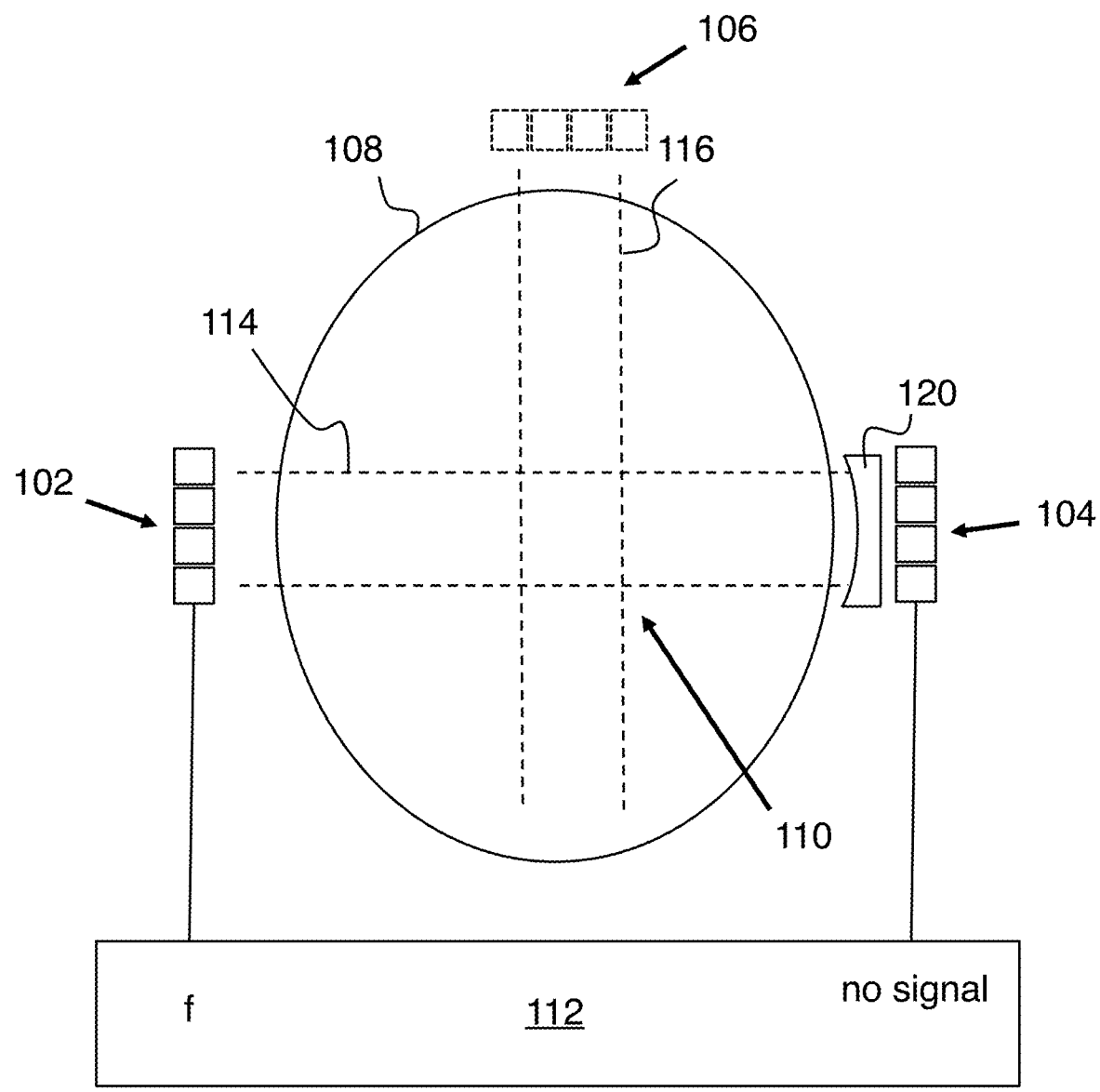

Optionally the apparatus can provide a third operating mode that is an impulse mode with only one of the two or more acoustic transducers activated. FIG. 1C shows one example of this possibility, where only transducer 102 is energized and a reflector 120 is used to provide interference in beam line 114. Alternatively, reflector 120 can be omitted. Thus the apparatus can further include one or more acoustic reflectors configured to reflect acoustic radiation emitted from at least one of the two or more acoustic transducers, wherein reflected acoustic radiation is focused by the one or more acoustic reflectors at or near the region of the patient.

Preferably, the two or more acoustic transducers include two diametrically opposed acoustic transducers, as in the examples of FIGS. 1A-C. This is the case considered in detail below. However, adding additional transducers can be helpful. In particular, two opposed transducers generates the largest radiation force, while two orthogonal transducers generates the smallest focal volume. Thus having a third transducer roughly orthogonal to two diametrically opposed transducers can get the best of both worlds—relatively high radiation force combined with relatively small focal volumes. However, transducers need not be diametrically opposed or orthogonal to practice the invention. Any angles between the transducers can be used, provided there is a region of beam overlap in the patient where interference can occur.

Figure 2A:
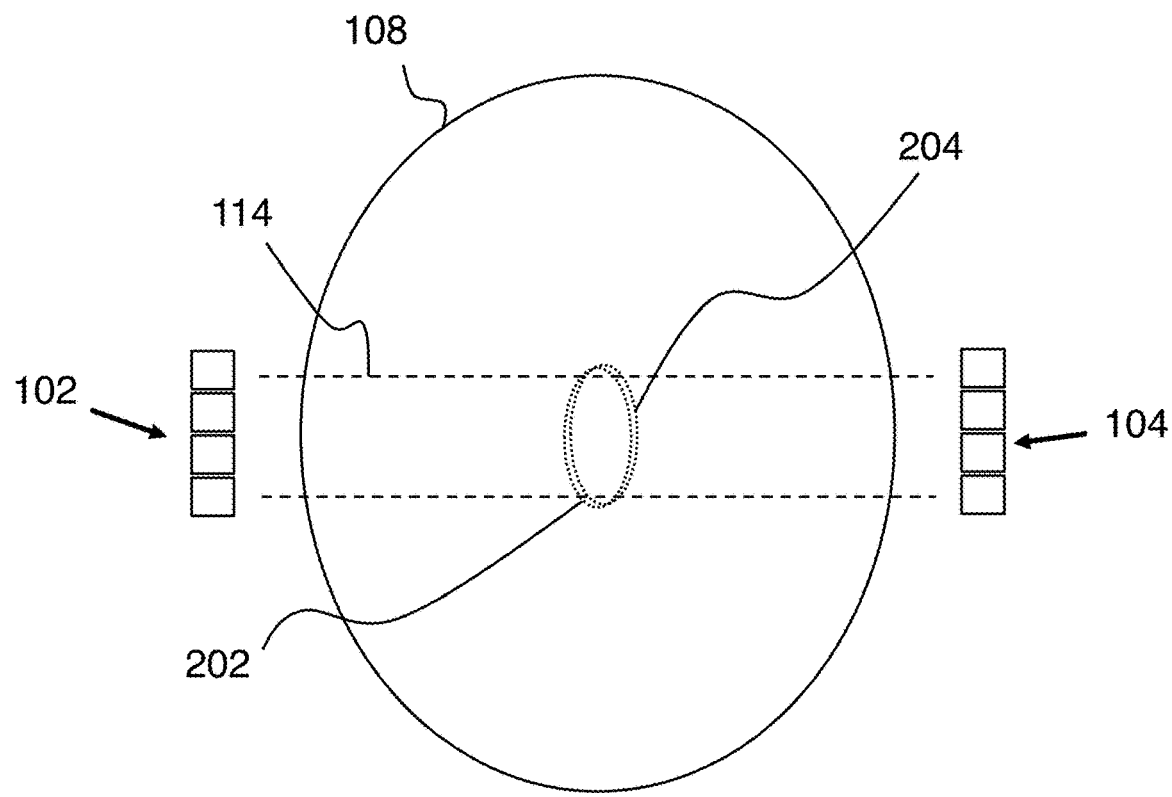
FIGS. 2A-B show two acoustic focusing configurations.
Figure 2B:
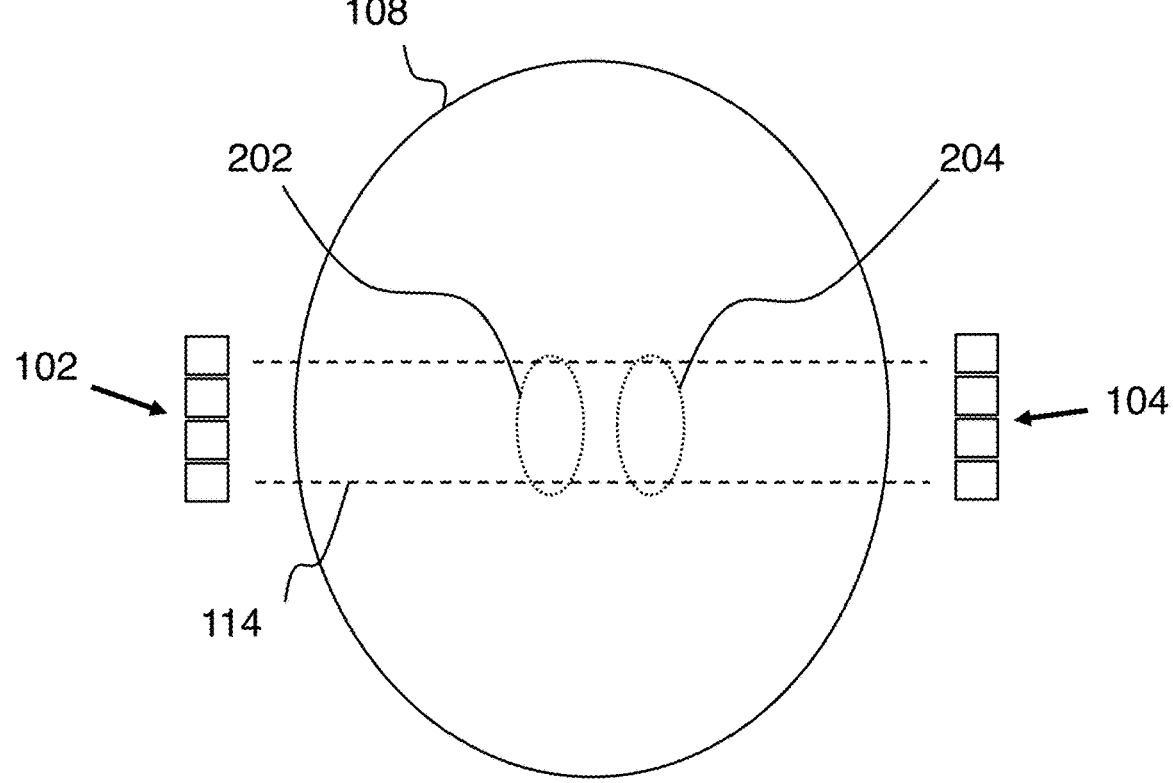

FIGS. 2A-B show two options for acoustic focusing. A first of the two or more acoustic transducers can be configured to provide focused ultrasound having a first focus region, and a second of the two or more acoustic transducers can be configured to provide focused ultrasound having a second focus region. FIG. 2A shows an example of the first focus region and the second focus region substantially coinciding. Here 102 and 104 are the first and second transducers, respectively, and 202 and 204 are the first and second focus regions, respectively. FIG. 2B shows an example of the first focus region 202 and the second focus region 204 being separated which can enhance neural activity modification between the first focus region and the second focus region.

A2) Summary of Theory of Ultrasonic Neurostimulation

Thus far, ultrasonic neurostimulation has been performed without a detailed understanding of the responsible mechanisms. Although stimulation methods have been improved by systematically varying stimulus parameters, in practice, the number of parameters that can be changed is very large. It is not practical to try all possibilities, in all animal models, and in all possible applications, to find the optimal stimulus for any given situation. Typically, ultrasonic neurostimulation stimuli either replicate parameters that have been published, or a few parameters are varied until an improvement is observed. Achieving an optimal stimulus (obtaining the greatest therapeutic effect with minimal delivered energy) requires an understanding of the mechanism by which ultrasonic neuro-stimulation functions. We provide a theory of ultrasonic neuro-stimulation from which we derive an optimal stimulation method.

Ultrasonic acoustic pressure waves oscillate at frequencies too high to have a direct effect on biological tissue. When acoustic wave energy is absorbed or reflected, there is a transfer of momentum that results in a static force known as radiation force, a phenomenon common to all kinds of waves, including light. This radiation force does not oscillate at the acoustic frequency, rather it remains constant so long as the ultrasonic stimulus is on. The strength of this radiation force is determined by the intensity of the acoustic pressure wave and the amount of energy that is absorbed or reflected. It is well known that this force can physically move tissue on the order of microns without harming patients. The physical displacement from radiation force puts stress on tissue and this stress is converted into electrical activity in neurons most likely by mechanosensitive ion channels that are present in the nervous system. To optimize the efficiency and spatial specificity of neurostimulation the objective is to maximize stress caused by radiation force in the smallest volume. Experimental evidence in support of this theory is described in detail in section B below.

A3) Resonant Cavities and Standing Waves

It is known that acoustic resonators can be built that will exert mechanical forces on small objects such as single cells to manipulate them without harming them. This field is known as acoustofluidics. It is a useful technology to manipulate single cells into a particular location for some kind of measurement. These resonators are built with specific dimensions matched to the acoustic frequency being used to establish standing waves. These standing waves are created either with single transducer and a reflector or by having two opposing transducers (FIGS. 1C and 1A respectively). The distance between these elements is an exact multiple of half the wavelength. The standing wave that results from the interference of two waves generates alternating regions of high and low radiation pressure. Particles or cells are mechanically forced away from high pressure areas known as anti-nodes into the low pressures regions known as nodes. In this way cells are mechanically manipulated into a certain location for some kind of measurement. We will use this acoustic resonator idea for an entirely different purpose, to stimulate neurons. The acoustofluidics literature makes no mention of using a resonator for this stimulation of neural tissue. Neural tissue in the small high pressure areas will be stretched while neural tissue in the small low pressure areas will be compressed, achieving large amounts of stress in small volumes, which is our previously stated objective.

A4) Translating Experimental Results into a Clinical Device

The in vitro experimental condition does not mimic in vivo clinical conditions. The presence of the rigid MEA has a profound effect on our results and would not be present in vivo. However, we can duplicate the effect of the MEA in vivo by either using either a reflective element or a second transducer on the opposite side of the target tissue to make a resonant cavity and generate standing waves as shown conceptually in FIGS. 1A-C, but implemented on a much larger scale to obtain neural stimulation. An important idea of this work is to place transducer #1 on one side of the target tissue and either a reflector or another transducer on the exact opposite side of the transducer #1. For example, if the target tissue is somewhere inside the human brain, transducer #1 is placed on the head of an individual such that it is possible to place transducer #2 on the opposite side of the head so that the two beams fall along a single straight line that intersect at the target tissue creating an interference pattern in the target tissue. This is different from an array of transducers where the beams intersect at a variety of acute angles for the purpose of creating a smaller focal volume, not along a single straight line for the purpose of creating an interference pattern.

A5) Variations

This approach can be used on any part of the nervous system, central or peripheral, including all sensory systems. It might be used to stimulate, inhibit or modulate neural activity for the purpose of treating various nervous disorders, too numerous to explicitly list here. There are various ultrasound stimulation parameters such as carrier frequency, pulse repetition frequency, intensity, and pulse duration that might be varied to obtain optimal values for a given clinical condition. In the case of two transducers there are additional parameters that specify the relationship between the two transducers, such as phase. Furthermore, the second transducer may operate at a different carrier frequency from the first transducer and other parameters may be different. Although it is generally the case that the focal volume corresponds to the targeted neural tissue, that is not the case in version #3 described below.

Figure 10A:
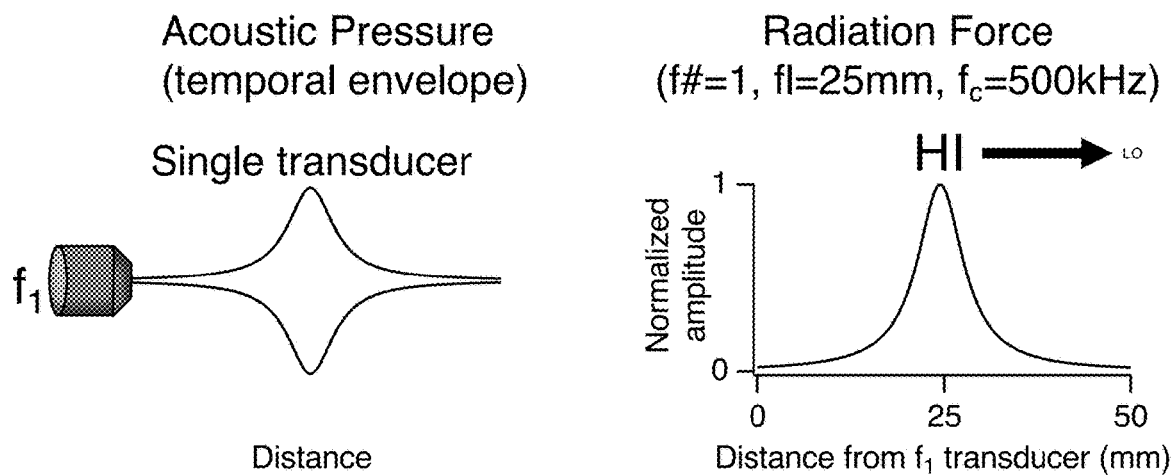
FIGS. 10A-B show exemplary designs for a pattern interference radiation force neural stimulator.
Figure 10B:
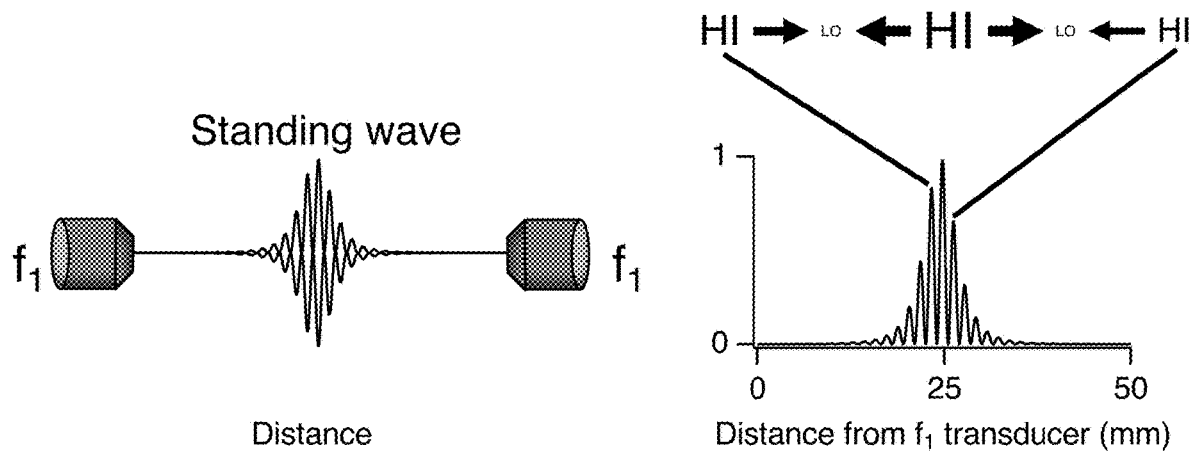

Exemplary embodiments include:

1) Standing wave version (FIGS. 10B, 1A, 1C). Here the goal is to create a standing wave in the target tissue directly analogous to our experimental results. This can be accomplished two ways. In one version a highly reflecting material (for ultrasound, such as metal) is placed opposite transducer #1 such that reflection off this material generates large standing waves in the target tissue but not outside the target tissue, which is accomplished by focusing the standing waves in the target tissue (FIG. 1C). The focusing is accomplished by the focusing lens of the transducer combined with the shape of the reflector. The second method is to replace the reflector with a second transducer operating at the same carrier frequency (but other stimulus parameters might be the same or they might be different, FIG. 1A). Thus large standing waves are created in the target tissue but not outside the target due to the focusing of the two transducers. The acoustic pressure from the standing wave is transformed into radiation pressure (FIG. 10B) generating alternating high and low pressure volumes that are separated by only wavelength/4.

2) Dynamic radiation force version (FIG. 1B). This is similar to the standing wave version with two transducers, except that the carrier frequencies are different for the two transducers. The difference frequency is generally much lower than the carrier frequencies, typically difference frequencies are on the order of 1 kHz to 100 kHz. Preferably this frequency range is 10 kHz to 100 kHz and more preferably it is 20 kHz to 100 kHz. This results in the vibration of the target tissue at this difference frequency (known as vibroacoustography in the ultrasound elasticity imaging literature. This vibration of the target tissue at the optimal difference frequency (to be determined experimentally) could produce more effective neural stimulation in some applications.

3) Offset focal volumes version (FIG. 2B). Instead of having overlapping focal volumes from the two opposing transducers, the focal volumes are offset so that the target tissue gets squeezed by the opposing focal volumes. So the target tissue lies in between the two focal volumes. This may be advantageous for certain applications.

4) Space-time dynamic radiation force versions (applicable to any of the above versions). Instead of having two temporally static carrier frequencies, we can vary both frequencies (substitute $f1(t)$ for $f1$ and $f2(t)$ for $f2$ in the above versions) in time to alter the radiation force in both space and time electronically. The temporal variation of frequency for the two transducers might be the same such that the difference frequency remains the same in time, or it might be different, so that the difference frequency itself varies with time. Likewise, the phases of the two carrier frequencies can be dynamically altered either to maintain a similar phase difference or to create a dynamically changing phase difference. This serves a similar function as changing the frequencies by permitting electronically controlled changes to radiation force in space and time.

B) Scientific Discussion

B1) Figure Captions

Figure 3:
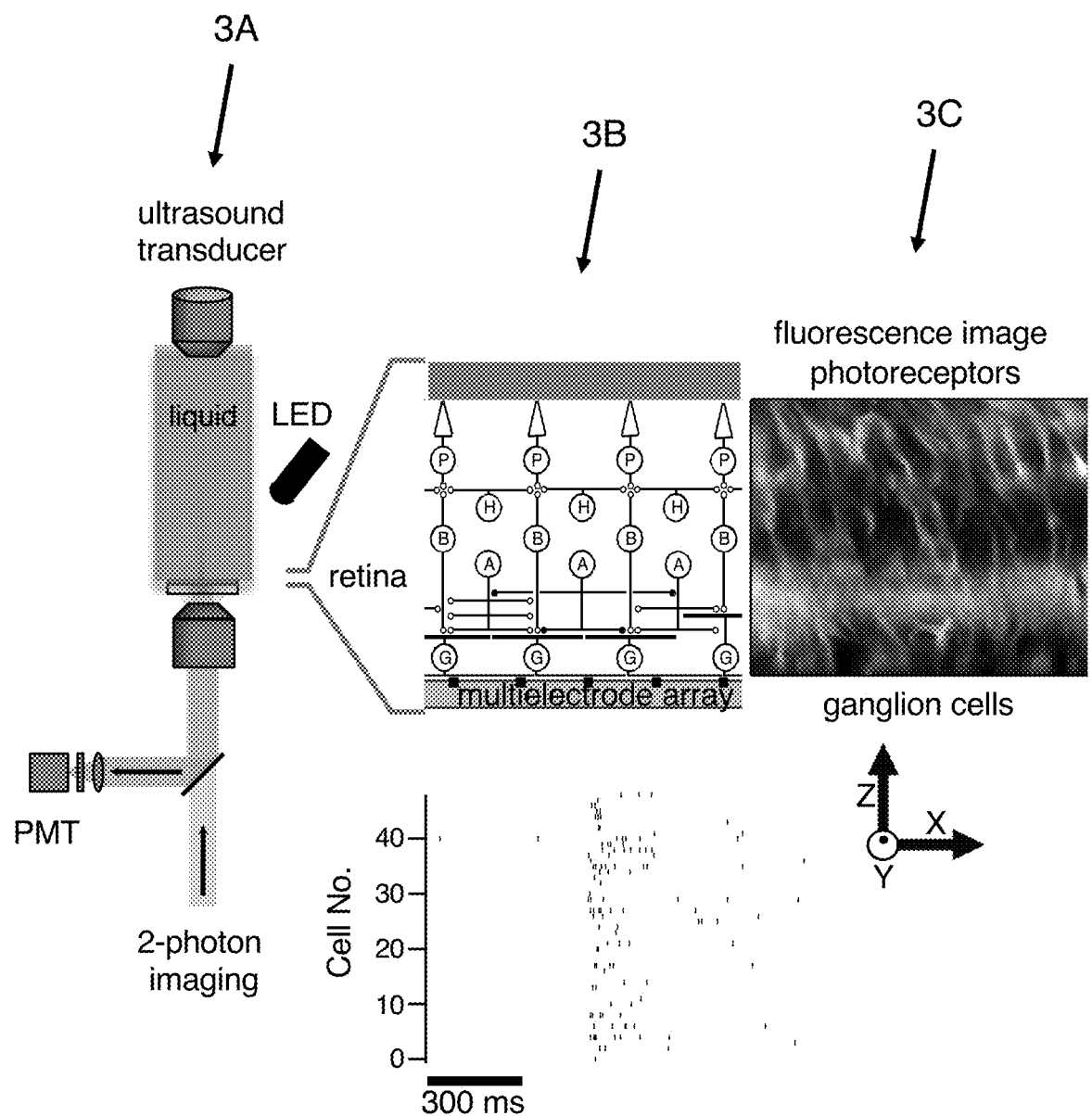
FIG. 3 shows an experimental configuration for the work of section B.

FIG. 3 shows the experimental configuration for ultrasonic stimulation and optical measurement in the retina. 3A is a schematic diagram of an ultrasound transducer mounted vertically and immersed in perfusion fluid with the focal point on the retina. Two-photon imaging is performed from below while a red LED from above can be used for visual stimulation. 3B, Top, Expanded view shows the retina placed ganglion side down on a multielectrode array (MEA) (P=photoreceptors, H=horizontal cells, B=bipolar cells, A=amacrine cells, G=ganglion cells). The ultrasound field spans the width of the entire retina. Bottom, A population of ganglion cell spiking activity recorded with an MEA in response to ultrasound. 3C shows a retinal image using the dye FM4-64 (showing cell membranes and processes) in a slice in the XZ plane.

Figure 4A:
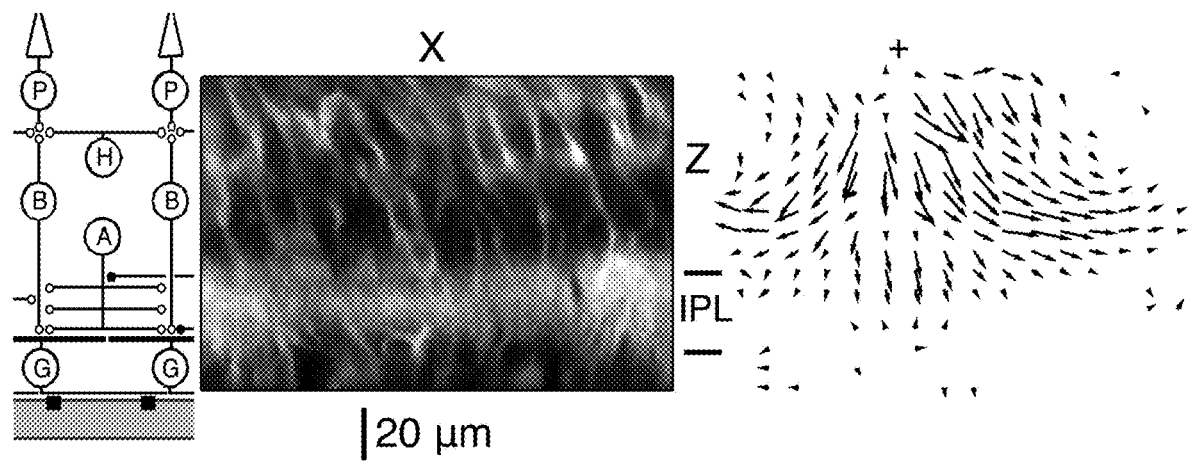
FIGS. 4A-B show displacement caused by acoustic radiation force.
Figure 4B:
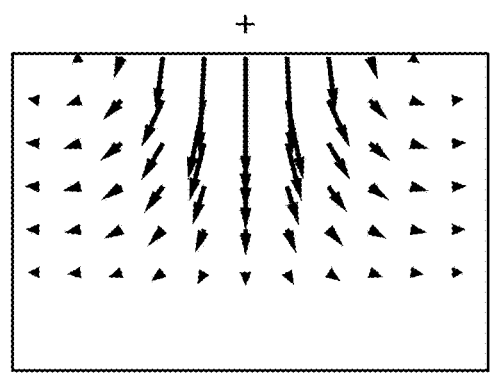

FIGS. 4A-B show that ultrasonic radiation force causes displacement in the retina at 43 MHz ($I_{SP}$=40 W/cm$^2$). FIG. 4A Left is a schematic of the retinal circuit aligned vertically with images to the right. FIG. 4B Middle is an XZ retinal slice image taken near the ultrasound focus. FIG. 4B Right is an XZ slice through a vector field showing displacement (relative magnitude and direction) resulting from ultrasonic stimulation. The cross indicates the center of focus. The vector field was computed from the image at steady ultrasound ON relative to ultrasound OFF. FIG. 4B shows the vector field of displacement using a simulation of radiation force acting on the retina, E (Young's modulus of elasticity)=0.5 kPa, maximum displacement is at center top (4 μm). Scale of vectors is different than the scale of the image. The cross is the center of focus.

FIGS. 5A-C show dynamics of ultrasonic displacement in the retina at 43 MHz ($I_{SP}$=40 W/cm$^2$). FIG. 5A Left is a schematic of the retinal circuit aligned vertically with images to the right. FIG. 5A Middle is an XZ image slice, where the white line indicates the spatial cross section which is then shown as a function of time at the right. FIG. 5A Right shows temporal changes during one second ultrasound OFF, one second ON, and one second OFF. FIG. 5B shows maximum downward displacement with the dialysis membrane in place. A Gaussian was fit to the bright spot in each 10 ms time bin and the mean position plotted as a function of time. FIG. 5B Top is a stimulus trace showing the timing of ultrasound onset and offset. FIG. 5B Bottom shows vertical displacement as a function of time. The relaxation after stimulus offset is shown fit with a double exponential. FIG. 5C shows maximum downward displacement without the dialysis membrane in the pathway.

Figure 6A:
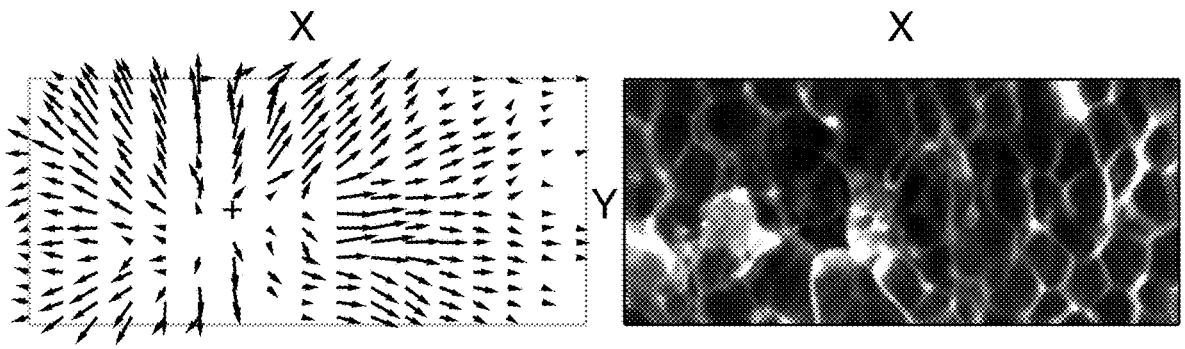
FIGS. 6A-C show the relationship between displacement and neural activity.
Figure 6B:
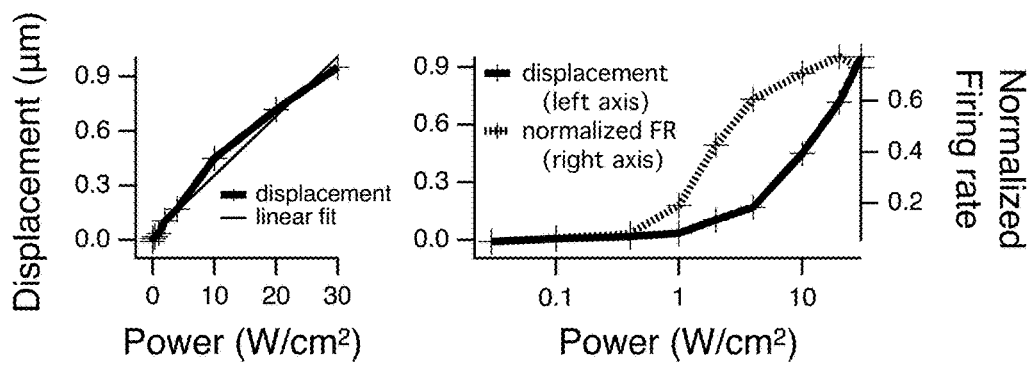
Figure 6C:
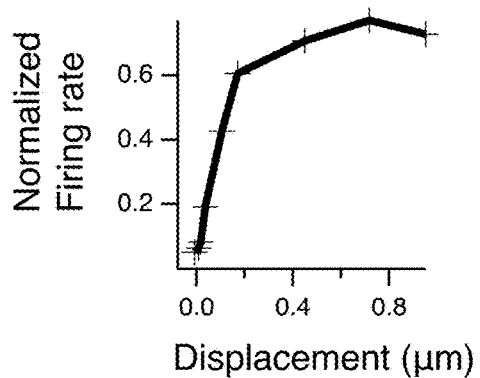

FIGS. 6A-C show the relationship between displacement and neural activity at 43 MHz. FIG. 6A Left is an XY slice through the focus (cross: point of minimal displacement) at a depth of maximal lateral displacement about midway through the retina that shows lateral displacement vector field in all directions moving away from the focal point. FIG. 6B Right is a corresponding XY slice image with ultrasound OFF. FIG. 6B Left shows maximum lateral displacement (in XY for a given depth) plotted vs. intensity. Data points are shown as "+", thin line is a linear regression fit ($r^2$=0.98). FIG. 6B Right shows normalized population firing rate (n=61) plotted vs. intensity and superimposed over displacement vs. intensity, where the x-axis is now on a log scale. FIG. 6C shows normalized population firing rate plotted vs. displacement from FIG. 6B for each intensity value.

Figure 7A:
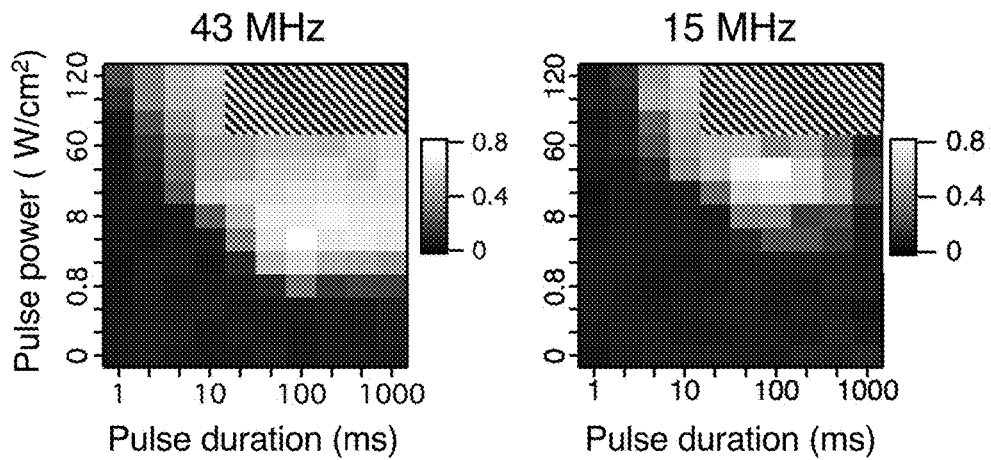
FIGS. 7A-D show the effect of frequency on ultrasonic stimulation.
Figure 7B:
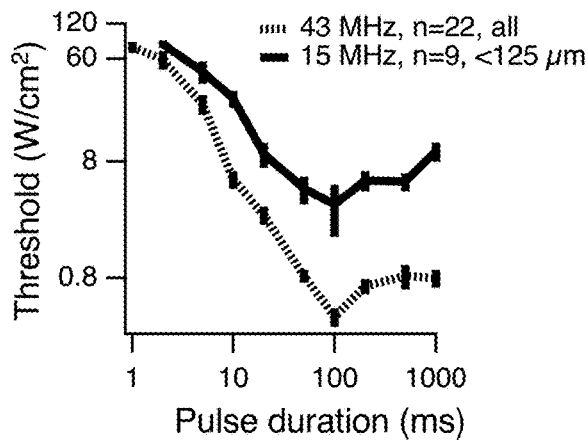
Figure 7C:
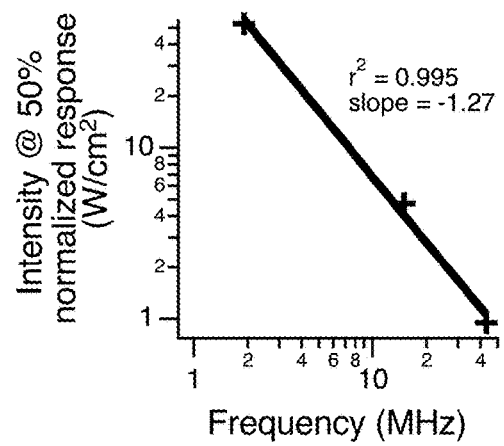
Figure 7D:
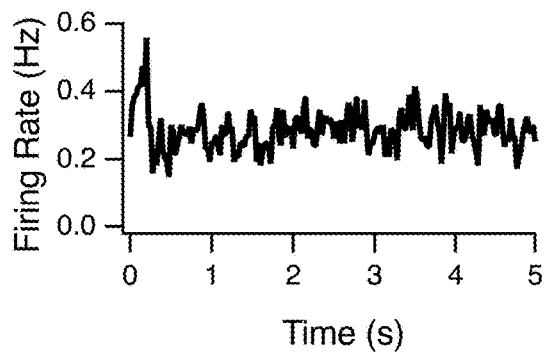

FIGS. 7A-D show that ultrasonic stimulation at higher acoustic frequency has a lower threshold. FIG. 7A Left shows normalized population (n=22) firing rate plotted as a function of intensity $I_{SP}$ and pulse duration for 43 MHz. Cross-hatching indicates parameters not tested. FIG. 7A Right is the same plot for 15 MHz for cells less than 125 μm from the focus (n=9). FIG. 7B shows threshold of stimulation as a function of pulse duration. More specifically, average thresholds across cells, (error bars are SEM) at each pulse duration are shown for 43 MHz and 15 MHz. FIG. 7C shows results from separate experiments, where normalized population responses were measured for three carrier frequencies (43 MHz, 15 MHz and 1.9 MHz, see FIG. 8C). The half maximal intensity is plotted against carrier frequency (black+). A linear regression line has a slope of −1.27 indicating that the exponent on frequency dependence is 1.27, this compares to a literature value of 1.18 that was used in the radiation force models of FIGS. 8A-C. FIG. 7D shows the population PSTH (n=75) generates a very weak response to ultrasound (100 ms ON starting at time zero, repeated every 5 seconds) for a 500 kHz transducer with $I_{SP}$=1.6 W/cm$^2$.

FIGS. 8A-C show that a radiation force model predicts responses in the retina. FIG. 8A (adapted from the literature) shows geometry for an analytic expression that was used to calculate radiation force in a cylindrical coordinate system based on transducer characteristics (a=radius of transducer, d=focal distance, f=frequency, I=intensity, x=axial distance, r=radial distance). FIG. 8B shows a radiation force model of retinal response. Cumulative radiation pressure at I=1 W/cm$^2$ is shown versus radial distance for the three frequencies. The radiation force is multiplied by a spatial weighting function, which in the retina is very small (~10 μm) and equivalent to the peak radiation force, and then passed through an optimized sigmoidal non-linearity to generate the model responses. FIG. 8C shows normalized population response for 43, 15 and 1.9 MHz as a function of intensity compared to the radiation force model output (n>20 cells in each case).

Figure 9A:
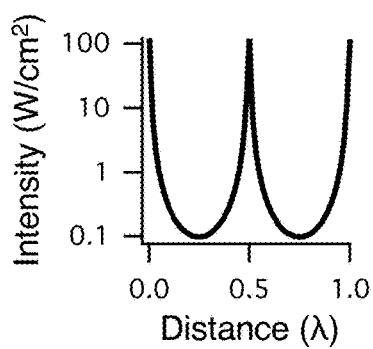
FIGS. 9A-E show the effect of standing waves on ultrasonic neurostimulation.

FIGS. 9A-E show how standing waves modulate ultrasonic neurostimulation. FIG. 9A is a COMSOL simulation at 1.9 MHz and a nominal intensity of 56 W/cm$^2$ (focal intensity in free space) of a transducer with an ideal reflective surface, demonstrating a periodic modulation in acoustic intensity as a function of changing transducer distance to the MEA expressed in wavelengths. The intensity plotted is the on-axis average values in the retina. Zero distance indicates the focal point of the transducer is coincident with the retina-MEA interface. Positive values of distance expressed in terms of wavelength indicate the transducer is moving further away from the MEA. An ideal reflective transducer is shown to illustrate the periodicity of modulation with distance, and a transducer with lower reflectivity as we used would produce a smaller modulation at the same period.

Figure 9B:
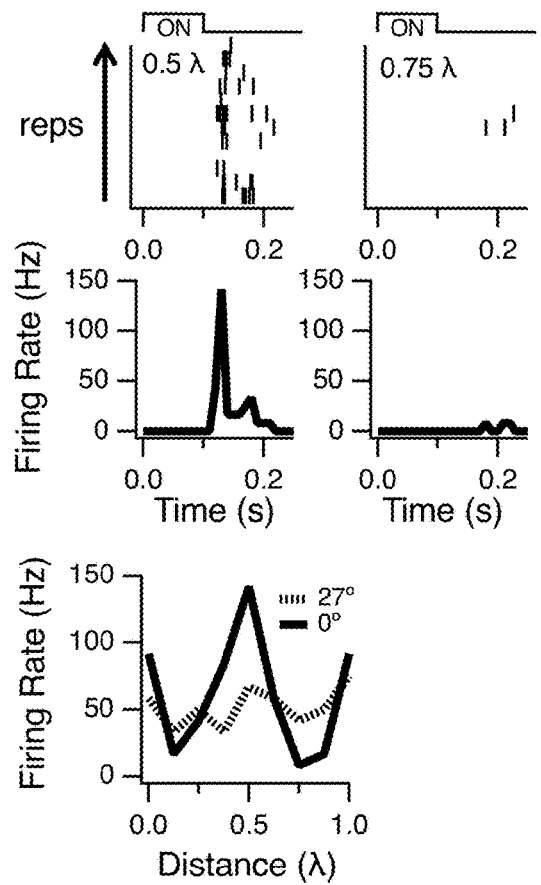
Figure 9C:
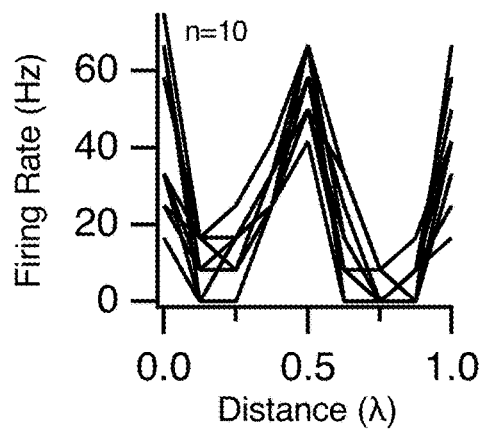

For the results of FIG. 9B a 2.25 MHz transducer was operated with a carrier frequency of 2.9 MHz ($\lambda$=517 μm). $I_{SP}$=155 W/cm$^2$, and a 100 ms pulse was repeated every 15 s for 12 trials. FIG. 9B Top shows Raster plots and PSTHs of the response of one cell when the vertically oriented transducer was moved a distance of 0.5$\lambda$ and 0.75$\lambda$. FIG. 9B Bottom shows peak firing rate response from this cell when the transducer was vertical (0°) showing strong modulation with a period of $\lambda$/2 as the transducer was moved away from the MEA. Distance is measured in terms of wavelength relative to a starting position, which was chosen to maximize the population response. Also shown is the response when the transducer was tilted at an angle of 27° relative to vertical (dotted line). FIG. 9C shows peak firing rate responses from ten other cells when the transducer was vertical demonstrating that many cells exhibit the same pattern of response with respect to transducer distance.

Figure 9D:
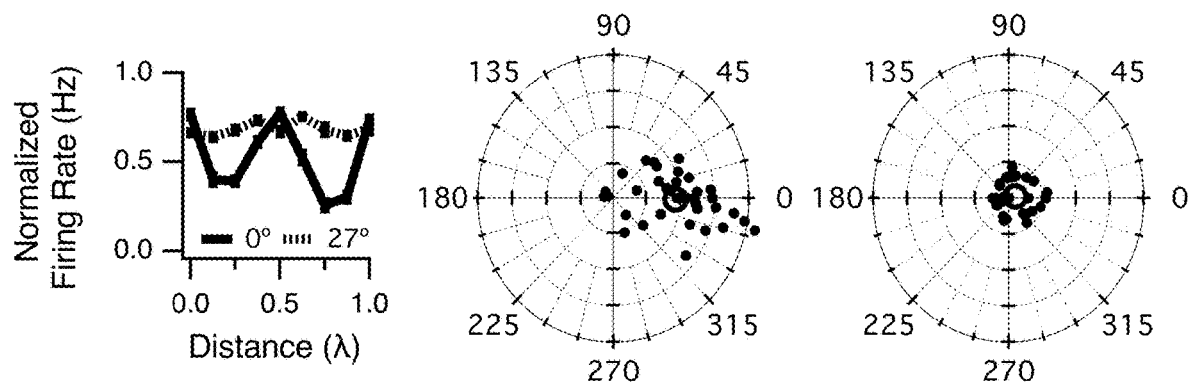

FIG. 9D Left shows normalized population response for vertical (0°, n=37) and tilted (27°, n=30) transducers. FIG. 9D middle shows the FFT of firing rate vs. distance. The amplitude and phase are shown at a frequency of 2 cycles/$\lambda$ for each cell that responds to ultrasound when the transducer is vertical (0°). In this plot, distance from the center represents the depth of modulation (normalized by the mean, linear scale) of the response by the transducer position at a period of $\lambda$/2. The angle is the phase of the 2 cycles/$\lambda$ Fourier component, reflecting the transducer distance at which the response was maximal. The circle shows the mean population response. Right, FFT of firing rate vs distance when transducer was tilted at 27°.

Figure 9E:
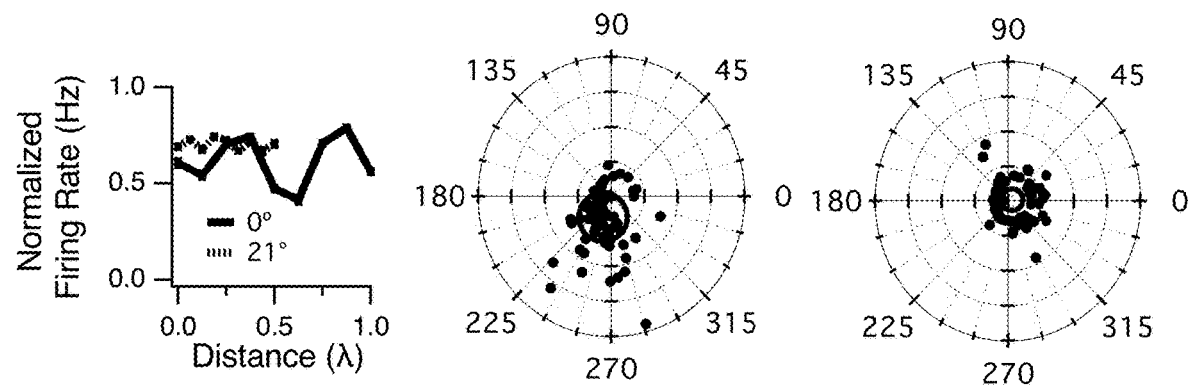

FIG. 9E Left is the same as FIG. 9D left except the 2.25 MHz transducer was operated at a carrier frequency of 1.9 MHz ($\lambda$=789 μm), and angle of the transducer when tilted was 21°, $I_{SP}$=95 W/cm$^2$ (n=90 for 0°, and n=78 for 21°). FIG. 9E middle shows the average phase differs from FIG. 9D because the transducer was not repositioned to set the peak response at the starting position. FIG. 9E Right shows that for the tilted condition (21°), the distance traveled was only one full cycle ($\lambda$/2) with smaller step sizes.

FIGS. 10A-B show design of Pattern Interference Radiation Force (PIRF) neural stimulator. On the left of FIGS. 10A-B are cartoons of acoustic pressure for various transducer configurations. Traces indicate the envelope of the acoustic pressure in time. The right sides of FIGS. 10A-B show radiation force in axial direction computed for a transducer of focal length 25 mm, f #=1 and carrier frequency=500 kHz, for the different transducer configurations. The black arrows indicate the direction and relative magnitude of radiation force from HI (high pressure region) to LO (low pressure region). FIG. 10A shows the simplest case of a single transducer. FIG. 10B shows radiation force for two transducers operating at the same frequency with overlapping focal volumes to generate a standing wave.

B2) Introduction

Ultrasonic neuromodulation has been demonstrated in the brains of human, monkey, sheep, rat, mouse, and retina of salamander and rat. The capability of ultrasound to reach any brain structure noninvasively through the skull, and the highly developed technology to deliver ultrasound make this approach promising both for basic studies of neural function and clinical applications. Yet results in different preparations have varied, including both excitatory and inhibitory effects. The development of this approach would benefit greatly from a quantitative understanding of the mechanisms of ultrasonic neuromodulation, allowing the process to be optimized in terms of efficacy of stimuli, efficiency and spatiotemporal distribution of effects.

In the process of transduction of a stimulus into a biological response, one can distinguish the physical mechanism such as acoustic pressure or thermal energy from the biophysical mechanism that senses that energy, including changes in membrane capacitance or particular ionic channels. Here we focus on the physical mechanism by which an acoustic wave is converted into an effective stimulus for a neuron, a process that is currently not understood. The leading candidates for physical mechanism are radiation pressure, the process by which an absorbed or reflected wave delivers momentum, and cavitation, which includes the stable or unstable formation of bubbles, creating a mechanical disturbance, and thermal energy.

Radiation force is a nonlinear effect proportional to the acoustic wave amplitude, thus creating a continuous, non-oscillating force for a stimulus of constant amplitude. By this mechanism a carrier wave with a frequency too high to have a direct biological effect can be converted into a low frequency mechanical force with dynamics of the envelope of the wave. When radiation force is exerted on a liquid, this results in bulk flow of fluid known as acoustic streaming. Tissue attenuation increases with carrier frequency, therefore radiation force and also heating will increase with frequency.

Cavitation can occur if the acoustic pressure wave becomes sufficiently negative, causing gas bubbles to form that oscillate at the carrier frequency. Inertial cavitation occurs when those oscillations change in size and eventually burst the bubble, creating a destructive violent event. In stable cavitation the bubble does not burst and is hypothesized to produce safe neuromodulation. Cavitation is less likely at higher carrier frequencies because it becomes more difficult to sustain oscillations in the bubble.

In this study we use optical imaging to measure displacements in the retina and vary the acoustic frequency to test which of these mechanisms is most likely. We find that ultrasonic stimulation in the retina is consistent with a model whereby radiation force produced micron-scale mechanical displacements. The acoustic frequency dependence is consistent with radiation force but inconsistent with cavitation. In addition, we see that standing waves influence the effects of ultrasound. We conclude that radiation force is the primary physical mechanism for ultrasound to stimulate the retina.

B3) Materials & Methods

B3a) Experimental Design and Statistical Analysis

We conducted several different types of experiments for the purpose of establishing whether radiation force is the dominant physical mechanism responsible for ultrasonic neurostimulation, the details of these experiments are described below in the appropriate sub-sections. In terms of experimental design, our goal is to use at least two retinas from two different salamanders and record from at least 30 ganglion cells for electrophysiology experiments. For the imaging experiments we used three retinas from three salamanders, for the 43 MHz electrophysiology we used three retinas from three salamanders, for 15 MHz recordings we used two retinas from two salamanders, and for lower frequency recordings (2.9 MHz, 1.9 MHz and 500 kHz) we used two retinas from two salamanders. For electrophysiological recordings the number of cells for each experiment is indicated either in the figures or in the figure legends. Data is available upon request.

All statistics used have well known definitions and require no additional information (e.g., mean, standard error of the mean, squared Pearson correlation coefficient $r^2$).

B3b) Electrophysiology

Multielectrode array (MEA) recordings were performed as described in the literature. The isolated retina of the tiger salamander of either sex was adhered by surface tension to a dialysis membrane (Spectrapor 7 50000, Fisher Scientific) attached to a custom Delrin holder. The holder was placed on a motorized micromanipulator (MP-385-2, Sutter) and lowered onto a multielectrode electrode array (ThinMEA, Multichannel Systems) ganglion cell side down. For 43 MHz experiments where the focal spot <100 µm, a high-density array was used (5×6, 10 µm diameter electrode, 30 µm spacing). For all other lower frequency experiments, a lower density array was used (8×8, 10 µm dia., 100 µm spacing), which better matches the focal spot size. Full field flashes from a red LED were sometimes used to verify that ganglion cells were responding normally to visual stimuli, especially if conditions of ultrasound stimulation did not show a response. Error bars are SEM unless otherwise noted.

B3c) Ultrasound Transducers and Stimuli

We used four different transducers, 43 MHz (custom), 15 MHz (Panametrics, A319S, 0.5" dia., 2" FL), 2.25 MHz (Olympus, V305) and 0.5 MHz (Olympus, V301) in order to span a large frequency range. The 2.25 MHz transducer had a relatively wide bandwidth and was operated at multiple frequencies (1.9 and 2.9 MHz). Transducers (15, 2.25 and 0.5 MHz) were fitted with a water-filled cone that was sealed with either parafilm (2.25 and 0.5 MHz) or plastic wrap (15 MHz) and mounted on a motorized micromanipulator (MP-385-2, Sutter). A camera from below was used to position the transducers so that the center of the focal spot was in the center of the array. Transducers were lowered into the bath above the retina, and height was adjusted so that the focal point was on the retina. Ultrasound propagated from the transducer, through the water-filled cone, perfusion fluid, dialysis membrane, retina, and then reflected off the glass/metal surface of the MEA (3A on FIG. 3). A function generator (model 8116A, Hewlett-Packard) provided the carrier frequency that was gated by the analog output of a National Instruments DAQ board. This signal was amplified by a 50 dB RF power amplifier (model 320L, Electronic Navigation Industries) and fed into the transducer. A hydrophone was used to measure power output from the water-filled cones into a tank of water as a function of three spatial dimensions, except for 43 MHz, which is too high for a conventional hydrophone, and for which power was extrapolated from hydrophone measurements at 20 MHz. All power measurements are the spatial peak, $I_{SP}$, because with a 100% duty cycle (continuous wave) $I_{SPPA}=I_{SPTA}$ (i.e., pulse average=temporal average) in free space (water tank). These free space hydrophone measurements are not corrected for the reflection off of the MEA under experimental conditions and the resulting standing wave. The free space measurements we have provided are useful for reproducing our results and making relative comparisons across carrier frequencies. However, these measurements do not accurately describe the actual power distributed in space under experimental conditions where we have standing waves between the transducer and the MEA. Ultrasound transducer characteristics such as numerical aperture, efficiency, and acoustic impedance matching will all play a role in determining the standing waves that result from reflection off the MEA. Continuous wave is used for all experiments, so the only relevant parameters are carrier frequency, power, pulse duration, and repetition rate, which are given for each experiment.

B3d) Imaging

The styryl dye FM4-64 was bath applied by immersing the isolated retina in a concentration of 82 µM (100 µg in 2 ml) FM4-64 in oxygenated Ringer's for one hour prior to placement on the MEA. This dye inserts itself in the outer leaflet of the cell membrane where it becomes fluorescent, allowing us to image changes in position and shape of the cell membrane with ultrasonic stimulation.

A custom two-photon laser scanning microscope in the inverted configuration was used to image the retina during ultrasonic stimulation. A simplified diagram is shown in 3A of FIG. 3. Excitation at 970 nm from a Ti:sapphire laser (Tsunami, Spectra-Physics) was focused on the retina by a x40 1.2 NA (Zeiss) objective and the epifluorescence passed through an emission filter (FF01-725/150-25) and laser-light blocking filter (Semrock, FF01-680/SP-25), which was then collected by a PMT (H7422-P, Hamamatsu). The imaged area was selected to cover the ultrasound focal spot. We recorded a frame of 512×128 pixels at a rate of 18.6 frames per second for 1000 frames at one level in the retina. We started at the MEA and collected images in one µm steps for a total of 120 microns, covering the entire retina in depth, imaging 1000 frames at every step. The average laser power was set to 10 mW. ScanImage (now supported by Vidrio Technologies) software was used to record images.

The mirror position of the scanning galvanometers was recorded on the same computer that generates and records the ultrasound stimuli (one second on, one second off, 40 W/cm$^2$), allowing us to compute the timing of the image at any pixel relative to the ultrasound stimulus. The laser scanning and ultrasound stimulus were desynchronized, such that any given pixel will be recorded at random times during the two second period of ultrasound stimulation. In theory we can get temporal resolution approaching the dwell time of a single pixel with a sufficiently large data set; in practice we binned the data in 10 ms bins for a sufficient signal-to-noise ratio. To compute vector fields reflecting the effect of ultrasound, we used unwarpJ, which is an imageJ plug-in that performs spline-based elastic registration of two images. We compared steady state images in the ultrasound on and off conditions.

Because of the large area of scanning at a high frame rate (20 Hz), we corrected for most distortion at the edge of the frame by computing the average actual mirror position based on control experiments recording mirror positions with slow mirror velocities and no distortion and then recording actual mirror positions at high velocities. This distortion does not affect our analysis, which is based on changes in the images as a function of time in the cycle of ultrasonic stimulation.

B3e) Modelling Radiation Force to Explain Retinal Displacement

To model the observed displacement as an effect of radiation force, we assumed the ultrasound field at 43 MHz was transmitted through a multilayered medium composed of water, retina, glass, and air, and calculated assuming 40 W/cm² incident power. The retina layer was 150 um thick and the glass layer was 180 um thick. Water and air media were assumed to be half-spaces. The model includes the following: acoustic streaming (the bulk flow of fluid from radiation force acting on the liquid medium between the transducer and the retina), radiation pressure on the retina-water and retina-glass interfaces, radiation pressure from absorption in the retina, and the interference pattern that is a consequence of wave reflection off the MEA. The speed of sound and density parameters are standard values from the literature, the attenuation at 43 MHz was set at 4.01 dB/cm for water and 22.02 dB/cm for retina. Estimated radiation pressures were then used in COMSOL Multiphysics finite element software to calculate the deformation of the retina in response to ultrasound. The retina was considered to be an incompressible material (i.e., Poisson ratio of 0.5). We determined the value of the elastic modulus (0.5 kPa) that gives 4 μm of maximum displacement in the direction of the propagating wave as seen in the data. Since soft tissues such as retina exhibit large deformation with nonlinear strains, a large deformation model was used to estimate the displacement field in the retina.

B3f) Model of Standing Wave Amplitude as a Function of Transducer-MEA Distance

A COMSOL model to simulate standing waves was similar to the model described above except that after the incident wave reflected off the MEA, we allowed for that wave to perfectly reflect off the face of the transducer. In this case, retinal deformation was not calculated. The frequency is set to 1.9 MHz and the nominal intensity is 56 W/cm² (intensity at the focus in free space). Standing wave amplitudes were calculated by averaging intensity values on-axis in the retina. Zero distance refers to the reference position where the focal point is coincident with the retina-MEA interface.

B3g) Modelling Radiation Force to Explain Retinal Neural Activity

A quantitative radiation force model was used to fit neural population activity in the retina. The model is based on analytic equations valid for linear low-amplitude ultrasound in free space from the literature. This model does not account for the reflection off of the MEA and the resulting standing waves, the presence of coupling cones, and the dialysis membrane. For 1.9 MHz, where standing wave effects are large, we use the data from the transducer position with the lowest threshold. The analytic expression takes as input the absorption coefficient (retina is similar to brain, so we used a brain absorption coefficient value from the literature), the carrier frequency (f), intensity (I), radius of the transducer (a), and focal length (d), to estimate radiation force in three-dimensional space expressed in a cylindrical coordinate system where x is axial distance from the transducer and r is the radial distance away from the central axis. Radiation force weighted unit volume ($\Sigma w(x,r)RF(x,r)$, 10 μm grid in cylindrical coordinates, approximately the size of cell somas) is summed over a volume defined by three parameters: between two radii $r_1$ and $r_2$ and depth, and then passed through a sigmoid. The optimal values for salamander retina were determined to be the smallest possible volume around the focus $r_1=0$, $r_2=5$ μm, depth=10 μm, equivalent to the maximum radiation force. (FIGS. 8A-C). Units of radiation force at any point in space are in dynes/cm³. Free parameters (location and volume of summation and sigmoidal parameters) were found by minimizing the total rms error between the data and the model. FIG. 8B shows an intermediate stage of the model for I=1 W/cm². Radiation force is integrated along the optimal depth dimension (for retina 10 μm and for brain 2.5 mm) yielding cumulative radiation pressure as a function of radius r for different frequencies.

B4) Results

B4a) Radiation Force Causes Physical Displacement within the Retina

Ultrasonic stimulation was applied to a preparation used for measuring neural activity consisting of the retina placed on a planar multielectrode array (MEA) patterned on a glass slide (180 μm thickness). We imaged the retina through the glass MEA with a two-photon laser-scanning microscope after applying the membrane dye FM 4-64 to the bathing medium (3A on FIG. 3). A stack of images was recorded from the MEA up to the photoreceptor level while repeatedly stimulating the retina with ultrasound (43 MHz carrier, one second on, one second off, at a power level known to cause strong neurostimulation ($I_{SP}$=40 W/cm²). The ultrasonic stimulation and scanning laser were uncorrelated, allowing all points in the volume to be imaged relative to the onset of the ultrasound stimulus, though on different trials. Using the time that the laser scanned each pixel, we reconstructed a movie of the average intensity at each pixel for the entire volume at a 10 ms resolution with respect to the ultrasound stimulus. At the onset of ultrasound, a sudden displacement toward the MEA was observed that lasted the duration of the stimulus.

We converted these displacements between steady-state On and Off ultrasound into a vector field using image processing software (see Methods) (FIG. 4A). The vector field, which was consistent with qualitative observations from the movie, showed that displacement was centered at the ultrasound focus, was greatest in the outer retina, and decreased to zero near the ganglion cell layer. Lateral to the focal point, displacement direction became progressively more lateral. Other fluctuations in displacements were observed that could be a consequence of inhomogeneity in the retina such as differing mechanical properties of inner plexiform layer and cell body layers.

To interpret the potential mechanism of this displacement, we modeled the expected mechanical response of the retina from radiation force using finite element analysis (COMSOL). In the simulation we considered the following factors: acoustic streaming (the bulk flow of fluid due to radiation force acting on a fluid), reflection from the water-retina and retina-MEA interfaces, absorption in the retina, and the interference pattern that results from the wave reflecting off the MEA. It was determined that 88% of displacement can be accounted for by the combination of reflection from the water-retina interface combined with the interference pattern (i.e., standing wave) that comes from wave reflection off the MEA, 9% comes from absorption, and 3% from acoustic streaming. A key parameter for this calculation is the Young's modulus of elasticity for the retina. However, the literature has values that vary by three orders of magnitude, depending on the method of measurement. We thus allowed the Young's modulus to be a free parameter and fit the model to account for the maximum observed displacement, which was 4 microns. The resulting value of Young's modulus was 0.5 kPa, which is close to the range found in the retina (0.1-2.0 kPa) with the scanning force microscopy method. The general features of the simulated vector field qualitatively matched the experimental vector field of displacement: large downward motion in the outer retina right under the focus which decreases to zero at the level of the MEA (FIG. 4B). In the simulation, the retina was modelled as a homogeneous medium, so features such as the large change in displacement at the boundary of the IPL were not captured.

To quantify the displacement, we found a region with high image contrast with the largest displacement and examined the change of displacement in 10 ms time bins (FIG. 5A). In a normal experiment, an optically clear dialysis membrane is used to hold the retina down against the MEA to facilitate ganglion cell recordings. Under this condition we observed a maximum of about 2 μm of displacement in the downward direction of the incident ultrasonic wave (FIG. 5B). Since we do not know the acoustic properties of the dialysis membrane, we were concerned that the displacement was caused by radiation force acting on the membrane. We performed an experiment with a hole cut into the dialysis membrane so that there was only Ringer's solution between the transducer and the retina. Under this condition, the displacement was significantly larger, 4 μm (FIG. 5C).

The vertical displacement occurred very rapidly (<10 ms) consistent with the expected temporal dynamics of radiation force. The fast onset of displacement is consistent with the fast response of neurons to ultrasonic stimulation. The recovery to baseline, which reflected the elastic properties of the retina was slower and was fit by double exponential with time constants of 33 ms and 530 ms (FIG. 5B) and 21 ms and 304 ms (FIG. 5C).

B4b) Relationship Between Displacement and Ultrasonic Neurostimulation

To examine the relationship between displacement and neural activity, we then compared measurements of these two quantities as a function of stimulus intensity. We imaged a level in the retina above the IPL midway through the retina that showed considerable lateral displacement. We varied the ultrasound intensity from below the threshold of neural activation to above the level of a saturating response (FIGS. 6A-C). We computed the displacement at this level as a function of ultrasound intensity and compare this relationship to that of the normalized firing as a function of ultrasound intensity taken from a different preparation (FIG. 6B). Neural activity was observed at a threshold of 1 W/cm$^2$, a level at the threshold of detectability of tissue displacement. The shapes of the two curves were different, with displacement increasing approximately linearly with stimulus intensity, and neural activity having a saturating dependence on intensity that was sigmoidal on a logarithmic scale. For each intensity value we plotted the normalized firing rate vs. displacement (FIG. 6C). There was a rapid increase in firing over submicron values of displacement, after which neural activity saturated. This indicates that submicron scale displacement was correlated with neural activity and gives a scale for the biophysical mechanisms that could transduce these displacements to produce activity.

B4c) Dependence of Neural Response on Acoustic Frequency

Absorption increases with higher acoustic frequency, and thus both radiation force and heating are expected to increase with higher carrier frequency. In contrast, the probability of cavitation decreases with higher carrier frequency because of the shorter time interval available to cause a bubble to form out of solution and to keep it oscillating. Many protocols of ultrasonic neurostimulation use lower frequencies (<1 MHz) to allow sufficient energy to penetrate the skull, which is known as transcranial neurostimulation. It is conceivable that at lower frequencies a different mechanism such as cavitation is involved. We therefore changed carrier frequency in several steps between 43 MHz and 0.5 MHz to measure activation of retinal ganglion cells by ultrasound at different frequencies on the retina.

To more completely characterize the response at a given frequency, we varied both pulse intensity and duration across a wide range for the 43 MHz transducer (FIG. 7A, Left). As the pulse duration was decreased below 100 ms, greater intensity is required to achieve stimulation (FIG. 7B). This relationship is consistent with the threshold being proportional to the integral of the pulse to obtain total energy, as is also found in electrical stimulation.

Using the same stimuli, at 15 MHz a greater intensity was required to stimulate neurons compared to 43 MHz (FIG. 7A). A 100 ms pulse duration was still optimal and this value was used as the default pulse duration in other experiments (FIGS. 7A-B). The increase in neural activity with increasing acoustic frequency was qualitatively consistent with radiation force, and inconsistent with cavitation as a mechanism. It's also inconsistent with in vivo mouse results which show that relatively higher frequencies (in the range: 0.3-2.9 MHz) require more intensity to stimulate neurons. We considered the possibility that for frequencies above some threshold (e.g., 15-43 MHz), radiation force is dominant; but for frequencies below some threshold (e.g., 0.3-2.9 MHz), cavitation is the dominant mechanism. To test these different mechanisms at different frequency range hypothesis and to resolve this paradox, we used the exact same transducer-amplifier combinations with carrier frequencies of 1.9 MHz and 500 kHz from the mouse in vivo experiments on our MEA ex vivo retina set-up.

We found that at 43, 15 and 1.9 MHz, the intensity at half maximal varied as a function of frequency raised to a power of 1.27 (FIG. 7C), close to the previously measured value of 1.18 in cat brain. Finally, at 500 kHz, at the maximum achievable spatial peak power with our transducer ($I_{SP}$=1.6 W/cm$^2$), responses of single cells to this stimulus could not be detected with significance and were only detectable when averaging across a population of neurons (FIG. 7D). The results at all frequencies tested are consistent with radiation force as the single physical mechanism across the entire range of frequencies used (0.5-43 MHz), indicating other physical mechanisms do not play a major role.

B4d) a Radiation Force Model Explains Retinal Ultrasonic Neurostimulation

We then tested whether retinal neural activity could be fit with a single quantitative model of radiation force across the range of intensities and frequencies tested. The model is structured to be the simplest possible that minimizes RMS error between the model and data. The neural response was assumed to be proportional to the sum of radiation force over some unknown volume followed by a sigmoidal non-linearity. We used an analytical model of radiation force valid for linear low-amplitude ultrasound in free space, which has absorption coefficient, the carrier frequency, intensity, radius of the transducer, and focal length as parameters, to estimate radiation force in three-dimensional space expressed in a cylindrical coordinate system. From this model, we computed the radiation force for each intensity, transducer and spatial location, and then passed this value through a stage of spatial integration representing the neural properties that sense ultrasound and then a sigmoidal function to predict neural activity. The free parameters of the model defined the volume of spatial integration and shape of the sigmoid, which was fixed across all intensities and acoustic frequencies. In the retina, the spatial integration was centered on the transducer focus, and the optimized scale of integration was small (10 μm diameter, 10 μm depth), which was equivalent to computing the maximum radiation force. This model showed that the analytically computed maximum radiation force could be used to predict the neural response from 1.9 to 43 MHz with a single sigmoidal neural activation function in the retina (FIGS. 8A-C).

B4e) Thermal Effects Likely do not Contribute to Ultrasonic Stimulation of the Retina We measured temperature rise under our experimental conditions using small (76 μm) thermocouples (J and K type, OMEGA) placed on the array with a retina held in place on top of the thermocouple. With the perfusion running as during ultrasonic stimulation, the temperature change is not measurable at 60 W/cm$^2$ and 15 MHz, and without perfusion, we measure only 0.1-0.2° C. increase. Small thermocouples suffer from sources of artifact such as ultrasound reflection off the thermocouple and conduction of heat away from the source and heating due to friction from radiation force moving the transducer relative to tissue. This latter artifact is much greater with pulsed ultrasound, where the thermocouple will oscillate at the pulse repetition frequency, whereas we are using continuous wave. We expect that these artifacts are minor as the thermocouple was attached to the bottom of the dish thereby reducing friction since the thermocouple cannot move. The ultrasound will reflect off the glass surface of the MEA in any event, so reflection off the thermocouple is not significantly different from the normal experimental condition. We found that perfusion removed heat much more effectively than the thermocouple wire, such that under normal conditions of ultrasound stimulation with perfusion running, we cannot measure any temperature rise from ultrasound. Although these studies do not categorically rule out thermal effects at a fine spatial scale, we find no evidence of significant thermal effects. Higher resolution spatial-temporal measurements of temperature changes in the future will be useful to examine if any thermal effects do exist.

B4f) Standing Waves

In the retinal preparation, below the tissue is a glass MEA of thickness 180 μm, followed by an air space. The top and bottom surfaces of the MEA create a large mismatch in acoustic impedance, which is expected to reflect ultrasound. Thus the space between the transducer and MEA may form a cavity that could generate a standing wave, where locations spaced at one-half the acoustic wavelength ($\lambda$) would experience destructive interference (nodes), and intervening locations experiencing constructive interference (anti-nodes). The acoustic pressure in the standing wave is converted into radiation pressure through absorption generating alternating high and low pressure volumes that do not temporally modulate at the carrier frequency. The relationship between acoustic pressure standing waves and radiation pressure is well known in micro-fluidics, where it is used to physically move small particles, including individual biological cells, to a desired location. Radiation pressure is greatest at anti-nodes and smallest at nodes, causing tissue at nodes to be compressed by adjacent high pressure anti-nodes and tissue at anti-nodes to be stretched by adjacent low pressure nodes. Such mechanical pressure on tissue could have an additional influence on neural activity. We tested the neural effects of standing waves by simply changing the distance between the transducer and the MEA. This will not change the locations of the nodes and anti-nodes as they are fixed by the carrier frequency, but the change in cavity length will affect the amplitude of standing waves, with a maximal standing wave amplitude when the cavity length is a multiple of $\lambda/2$. To illustrate this effect, we computed a COMSOL simulation of the transducer-electrode array cavity with a perfect reflection off the transducer face, which produced a large modulation in acoustic intensity in the retina with a characteristic period of $\lambda/2$ in transducer distance (FIG. 9A). At the spatial sampling of this stimulation, calculated radiation force was nearly perfectly correlated with acoustic intensity (r=0.9997, not shown). Our transducers are not perfectly reflecting, and it is not clear whether reflections are off the transducer face or from the face of a plastic coupling cone covered with parafilm. A more realistic simulation with less than perfect reflection would generate a smaller depth of modulation but the period would still be $\lambda/2$.

We tested the effects of standing waves at relatively low frequencies, 2.9 MHz ($\lambda$=517 μm, $\lambda/4$=129 μm) and 1.9 MHz ($\lambda$=789 μm, $\lambda/4$=197 μm), close to where most ultrasonic neurostimulation studies are conducted, yet high enough that we can still get robust responses, and where the $\lambda/4$ distance is large and comparable to the thickness of the retina (~120-150 μm). The ultrasound stimulus was a continuous wave 100 ms pulse, which we had previously found to be optimal at higher frequencies (FIG. 7B) and was very close to the 80 ms continuous wave pulse used in the literature for in vivo mouse stimulation. The stimulus was repeated every 5 seconds to minimize potential adaptation effects. A single 2.25 MHz transducer with relatively wide bandwidth was used for both frequencies, and intensities were measured by hydrophone separately at each frequency in free space.

We found that the firing rate of some cells was very strongly modulated by the distance between the transducer and the MEA with a period of $\lambda/2$, consistent with standing waves (FIGS. 9B-C). Across the population, we quantified the standing wave effect by computing the Fourier transform of the firing rate as a function of transducer distance and examining the amplitude at a frequency of 2 cycles/$\lambda$ as well as the phase angle of the response (FIG. 9D, at 2.9 MHz) relative to the starting position (0°, vertically mounted transducer) with the focus at the MEA and moving away from the MEA. The population showed that the response was modulated at a period of $\lambda/2$, consistent with a strong standing wave effect.

We then tested whether standing waves were necessary for neurostimulation by tilting the transducer at an angle of 27° to vertical. Although a spatial interference pattern still occurs between the incident and reflected waves, the depth of modulation will not be as great as when the transducer is positioned vertically, and such a pattern would move with distance between the transducer and glass. We found that the tilted transducer condition still generated a response (FIG. 9D), but the response modulation with distance was greatly reduced. At an angle of 27°, the average across the population showed a depth of modulation of 26 times less than when the transducer was vertical. We further tested that standing waves were also observed at 1.9 MHz, $\lambda/4$=197 μm, using the same transducer, and similarly found that the population response was modulated at a period of $\lambda/2$ and that this average effect on the population diminished when the transducer was tilted an angle of 21° (FIG. 9E). From these results we conclude that standing waves influence the response but are not necessary for stimulation.

B5) Discussion

Our results show that ultrasonic neurostimulation in the retina produces radiation force and micron-scale displacement. A quantitative model of radiation force across multiple acoustic frequencies and power levels indicates that radiation force is the likely physical mechanism of action. We further show that standing waves can modulate neural activity, suggesting a potential new method to further control activity.

B5a) Thermal Effects of Ultrasound

Estimates of temperature rise based on $I_{SPTA}$, pulse duration, density and specific heat capacity and absorption coefficient are very small (0.007° C.-0.04° C. for in vivo studies in humans and sheep. Furthermore, these methods assume all energy goes to an increase in temperature, and do not account for heat loss by conduction or convection, so the actual temperature rise should be lower. Previously, at 43 MHz and 30 W/cm², well above stimulation threshold, we could not measure a temperature rise with the perfusion running, although we could measure a 0.5 deg. C increase from prolonged stimulation without perfusion. In a literature study using *C. elegans*, mutants lacking thermosensitive receptors behaved like wild type animals, while mutants that lack touch sensory neurons have an impaired response to ultrasound. Together, there is no evidence for heating as a physical mechanism for brief ultrasonic neurostimulation.

B5b) Cavitation

We found using the same transducers, amplifier, frequencies and power settings that successfully stimulated in vivo mouse that in the retina, higher acoustic frequencies were more effective than lower frequencies, thus ruling out cavitation as a possible physical mechanism (FIGS. 7A-D, 8A-C). Cavitation can be measured with subharmonic cavitation detectors. To date, there is no study demonstrating the existence of cavitation in the brain using parameters for neurostimulation in the CNS. Cavitation requires gas bubbles; however, outside of the lungs and the digestive tract, biological tissue is generally bubble free. An in vivo sheep brain study with a 660 kHz carrier found that at least 12.7 MPa was required to measure a nucleation event with both passive and active cavitation detection; whereas threshold pressures for low-power ultrasonic modulation in vivo brain studies are much less than 1 MPa. In another study using in vivo rabbit brain, cavitation only occurred at the very high power of 2000 W/cm² at −1 MHz; showing obvious tissue damage.

A hypothesis of ultrasonic neurostimulation is neuronal intramembrane cavitation excitation (NICE), which is a theoretical model that has been fit to empirical results. The intramembrane cavitation hypothesis asserts that stable cavitation exists inside the cell membrane causing a change in cell capacitance that ultimately leads to action potential firing. Although this model has been fit to various in vivo experimental data, it does not describe our data because of the strong correlation between greater neural activity and higher ultrasonic frequency.

B5c) Pressure Phosphenes

It has been known since ancient Greece that mechanical deformation of the eyeball generates pressure phosphenes (the appearance of light when there is none). Although it is still not known which retinal cells are responsible, it is clear that mechanical force can result in ganglion cell activity. Studies with deformation of the cat eyeball showed that different ganglion cells respond through network stimulation, likely in the outer retina. Most importantly they conclude that mechanical strain is the cause, not retinal ischemia from high intra-ocular pressure. The authors speculated that inhibitory horizontal cells or amacrine cells, might be sensitive to strain because of their lateral connections. A phenomenon that has been known for thousands of years supports the concept of mechanical strain on neurons as the cause for this neural stimulation.

B5d) Potential Biophysical Mechanisms

Leading candidates for biophysical mechanisms are mechanosensitive ion channels, capacitive effects from mechanical deformation of the cell membrane, and direct effects on endocytosis/exocytosis. A simple biophysical mechanism that could transduce mechanical strain is a change in membrane capacitance, which can result from radiation force. Alternatively, stretching, compressing or bending of the cell membrane may cause the opening or closing of mechanosensitive ion channels, which are found in all parts of the nervous system. These serve different functions such as controlling osmotic pressure to guiding developing neurons. Sensitive channels that are good candidates to convert mechanical stress from ultrasound into neural activity include Piezo, TRAAK, TREK-1, and TREK-2. In a study expressing mechanosensitive ion channels in *Xenopus* oocyte, ultrasound was found to significantly influence membrane current of the potassium channels and had a small effect on the sodium channel. In *C. elegans*, ultrasonic neurostimulation requires mechanosensitive channels.

It is known that high static pressure will suppress synaptic activity. This is the physiological basis for High Pressure Neurological Syndrome (HPNS), a danger for deep-sea divers exposed to pressures greater than 1 MPa, but one from which divers fully recover without permanent damage. Potential mechanisms are differential activation of calcium channels, or a direct effect on exocytosis. In general, multiple mechanisms of ultrasonic neurostimulation could operate under different conditions, including stimulus parameters or type of tissue.

B5e) Implications for Sonogenetics

A recent approach to modulating neural activity is the genetic targeting of molecules sensitive to ultrasonic stimulation. Termed either 'sonogenetics' or 'acoustic mechanogenetics', such methods promise to create an alternative to optogenetic approaches that benefit from the depth of penetration possible with ultrasound as compared to light. Key to the design of such approaches is the knowledge of the physical mechanisms by which ultrasound can act. Ultrasound effects acting through radiation force as we have identified here could potentially be used to activate sonogenetic probes. In doing so, in any given tissue, mechanical sensitivity of sonogenetic probes should exceed the endogenous sensitivity to ultrasound.

B5f) Effects on Ganglion Cells

The large displacements in the outer retina shown in this study are consistent with ultrasonic activation of neurons in the retinal network, which provide inputs to the ganglion cells. Previously we observed that blocking synaptic transmission with $CdCl_2$ abolished ultrasonic neurostimulation, indicating that we were not directly stimulating ganglion cells. One might assume, therefore, that the biophysical mechanisms of transduction are not present in the ganglion cell soma or dendrites. However, our present results show that little displacement was observed in the ganglion cell layer (FIGS. 4A-B). Thus, it may be that the ganglion cell soma can be directly activated by ultrasound if appropriate mechanical strain is applied. Further studies varying the geometry of the recording setup to produce mechanical strain at the ganglion cell level will be needed to assess whether ganglion cells can be activated directly.

B5g) Comparison with Another Ex Vivo Retina Study

Another ex vivo retina study at 2.25 MHz in rats showed that neurons frequently exhibit multiple response peaks with a temporal pattern that varies with intensity. We have seen similar effects using 1.9 MHz. Our intensity levels at 1.9 MHz are about one order of magnitude greater those used in this other work which could be due to species differences in either mechanical properties or biophysical mechanisms. The rat retina contains blood vessels making it mechanically stiffer, and salamander retina somas are relatively large (15 μm dia.). Or there may be a different distribution of mechanosensitive ion channels.

B5h) Relationships to In Vivo Studies

Some kind of measurement technology is needed to verify where the ultrasound focus is actually located in the brain and what area of the brain is activated in order to make in vivo behavioral results interpretable. How likely is it that the activated brain region is off-target for in vivo rodent work? When determining the spatial location of the transducer that produces the highest probability of a behavioral response, large variability in this spatial map was found across mice when tested at relatively higher frequencies. This spatial variability most likely arises from the ultrasound focus targeting different areas of the brain in different mice, even when the external location of the transducer is intended to be the same.

In addition, the interpretation of some in vivo results is potentially confounded by the possibility of inadvertent stimulation of the auditory pathway when ultrasound is modulated in the range of audible frequencies. This modulation in the audible frequency range is not present if continuous wave (CW) stimuli are used. The challenge for future studies is to find that region of ultrasound stimulus parameter space that generates direct neurostimulation without the auditory confound. Our studies of the ex vivo retina are of course free from auditory effects, thus making it a useful system to study the parameter space of direct neurostimulation. Our exploration of the stimulus parameter space has shown that a CW pulse of relatively long duration (e.g., 100 ms, FIG. 7B) has the lowest threshold. Notably, for the in vivo mouse model a continuous wave pulse of 80 ms was determined to be optimal in a previous report. In the domain of CW pulses there are fewer stimulus parameters (duration, intensity, and spatial location of the transducer for in vivo experiments) making it relatively easier to cover the entire relevant stimulus parameter space as we did in FIG. 7A. The introduction of a PRF (pulse repetition frequency) increases the dimensionality of the stimulus parameter space by adding modulation frequency and duty cycle making it impractical to explore the entire stimulus parameter space in addition to the confound of stimulating hair cells in the cochlea.

One prior study used CW pulses of 10 ms or shorter, and although another study used 80 ms pulses, they were not CW (a pulse repetition frequency of 1.5 kHz is in the audible range). Neither study used longer duration CW pulses as we have done here. The difficulty in exploring such a large parameter space is a strong motivating factor to develop a theory of ultrasonic neurostimulation that can guide us to the optimal stimulus. One can view stimulation of auditory or vestibular organs as being an off-focus activated brain region where low frequencies will be more effective due to their larger focal volumes. Recent research has demonstrated how to avoid auditory stimulation by smoothing the sharp edges on a 80 ms CW pulse of ultrasound thereby eliminating the auditory brainstem response without affecting motor responses in normal hearing mice.

A number of studies have looked at standing waves in rodent skulls, by both measurement and simulation. The small skull size combined with sub MHz frequencies that are not well focused in the axial direction will generate standing waves as a consequence of reflections off the opposite side of the head. These uncontrolled standing waves have the potential to stimulate parts of the brain that were not targeted.

B5i) Pattern Interference Radiation Force (PIRF) Neural Stimulator

The conventional approach to ultrasonic neurostimulation is to use a single transducer with a focus at the target (FIG. 10A). This produces radiation force, maximal at the focus, that will tend to generate tissue displacement in the axial direction, as well as strain. Deriving from our observations that the ultrasound transducer and MEA create a cavity that generates standing waves that influence the response, we consider the use of two opposing ultrasonic transducers for ultrasonic neurostimulation. This geometry will compress neural tissue (at nodes) and stretch other tissue (at antinodes) thus maximizing strain at very low power. From the acoustofluidics literature it is well known that there are two basic methods for generating standing waves in a resonant cavity. A single transducer generates a wave that reflects off an opposing surface (equivalent to our ex vivo setup with the array being the reflective surface). Alternatively, one can use two opposing transducers which is much more practical for stimulating the in vivo brain. Two opposing transducers are also more versatile, giving independent control over carrier frequency, phase and temporal envelope. By generating a focused standing wave between two opposing transducers (FIG. 10B) the resulting high frequency oscillation (period $\lambda/2$) in radiation force will stretch tissue located at high pressure areas and compress tissue located in low pressure areas. With two opposing transducers the focal region will be defined by the physical location of the transducers, but if each transducer is replaced by a phased array of transducers, then the focal regions (potentially multiple foci stimulated at independent times) can be determined electronically. PIRF multi-focal stimulation with variable time delays could be useful to exploit synaptic plasticity to strengthen or weaken synaptic connections between different brain regions with all of the parameters under electronic control.

One ultrasonic neuromodulation study used two confocal transducers operated at 1.75 MHz and 2.25 MHz to generate a beat pattern at 500 kHz. However, a 500 kHz difference frequency is likely too large to be optimally effective. In comparison, vibro-acoustography generally uses difference frequencies in the range of 20 to 100 kHz to mechanically vibrate tissue via dynamic radiation force to measure elasticity.

B5j) Pulsed Radiation Force can Produce Confounds

Many published studies have claimed that "pulsatile" ultrasound (i.e., modulating the carrier with a square wave) is more effective stimulus than continuous wave, often with a PRF in the 1-2 kHz range, but no theoretical reason has been given to explain why. Studies showing that ultrasound can act through an auditory pathway also show that 1 kHz PRF was most effective. There is at least one report of normal human subjects with earplugs inserted hearing high-frequency tones that are correlated with the intensity and pulse repetition frequency of transcranial Doppler ultrasonic imaging. Although it is still unclear how activation of the auditory system might influence the many behavioral or neural recordings, our results suggest that radiation force would translate the envelope of stimulation, i.e. the pulse repetition frequency into a mechanical stimulus. The direct conversion of the envelope of the stimulus to a mechanical stimulus through radiation force could explain why pulse repetition frequencies in the audible range are chosen as being more effective. In vivo researchers should address this potential confound, such as by using deafened animals, using continuous stimuli, or smoothing the edges of ultrasound pulses to reduce audible frequency components. Other potential confounds to direct brain stimulation besides the auditory system are activation of the vestibular and somatosensory systems. Direct measurements of brain activity will be important as opposed to relying exclusively on behavioral outcomes.

B6) Conclusion

There exists a strong theoretical and empirical understanding of using radiation force to exert mechanical strain in the fields of acoustofluidics and elasticity imaging. Here we show a new application of these principles to ultrasonic neurostimulation. Our findings suggest that future approaches to ultrasonic neurostimulation should explore the parameter space defined by these alternative methods of generating radiation force. An understanding of the physical mechanism of action will allow studies in this area to pursue how radiation force might be manipulated to optimize stimulation in different applications and simultaneously provide insights into biophysical mechanisms.

The invention claimed is:

1. Apparatus for modifying neural activity, the apparatus comprising:
    two or more acoustic transducers configured to have their acoustic outputs overlap in a region of a patient under treatment;
    a controller configured to control operation of the acoustic transducers;
    wherein the controller is configured to allow a user of the apparatus to select from at least a first operating mode and a second operating mode;
    wherein the first operating mode is a standing wave mode, and wherein the acoustic outputs of the standing wave mode are at the same frequency;
    wherein the second operating mode is an oscillating mode where the acoustic outputs have pairwise frequency differences in a range from 1 kHz to 100 kHz,
    wherein the controller is configured to drive the two or more acoustic transducers independently of each other, whereby electronic control of an acoustic interference pattern generated by the two or more acoustic transducers is provided in the region of the patient;
    wherein the two or more acoustic transducers include two diametrically opposed acoustic transducers.

2. The apparatus of claim 1, wherein a first of the two or more acoustic transducers is configured to provide focused ultrasound having a first focus region, and wherein a second of the two or more acoustic transducers is configured to provide focused ultrasound having a second focus region.

3. The apparatus of claim 2, wherein the first focus region and the second focus region coincide.

4. The apparatus of claim 2, wherein the first focus region and the second focus region are separated to enhance neural activity modification between the first focus region and the second focus region.

5. The apparatus of claim 1, wherein at least one of the two or more acoustic transducers is an acoustic transducer array.

6. The apparatus of claim 5, wherein the acoustic transducer array is configured to alter a focus position of the acoustic transducer array using phase control of elements of the acoustic transducer array.

7. The apparatus of claim 1, wherein the frequency of the acoustic outputs in the first operating mode is time-varying.

8. The apparatus of claim 1, wherein the frequency of the acoustic outputs in the first operating mode is time-independent.

9. The apparatus of claim 1, wherein a relative phase of the acoustic outputs in the first operating mode is time-varying.

10. The apparatus of claim 1, wherein a relative phase of the acoustic outputs in the first operating mode is time-independent.

11. The apparatus of claim 1, wherein the pairwise frequency differences of the acoustic outputs in the second operating mode are time-varying.

12. The apparatus of claim 1, wherein the pairwise frequency differences of the acoustic outputs in the second operating mode are time-independent.

13. The apparatus of claim 1, wherein the pairwise frequency differences of the acoustic outputs in the second operating mode are selected to maximize dynamic radiation force in the region of the patient.

14. The apparatus of claim 1, wherein the apparatus is configured to modify central nervous system neural activity.

15. The apparatus of claim 1, wherein the apparatus is configured to modify peripheral nervous system neural activity.

16. The apparatus of claim 1, wherein the modifying neural activity comprises a method selected from the group consisting of: stimulating neural activity, inhibiting neural activity and modulating neural activity.

17. The apparatus of claim 1, wherein a third operating mode of the apparatus is an impulse mode with only one of the two or more acoustic transducers activated.

18. The apparatus of claim 1, wherein the apparatus further comprises one or more acoustic reflectors configured to reflect acoustic radiation emitted from at least one of the two or more acoustic transducers, wherein reflected acoustic radiation is focused by the one or more acoustic reflectors at the region of the patient.

* * * * *